(12) United States Patent
Haverkost et al.

(10) Patent No.: US 8,460,365 B2
(45) Date of Patent: *Jun. 11, 2013

(54) VENOUS VALVE, SYSTEM, AND METHOD WITH SINUS POCKET

(75) Inventors: Patrick A. Haverkost, Brooklyn Center, MN (US); Jason P. Hill, Brooklyn Park, MN (US); Susan M. Shoemaker, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 137 days.

This patent is subject to a terminal disclaimer.

(21) Appl. No.: 13/117,770

(22) Filed: May 27, 2011

(65) Prior Publication Data

US 2011/0230949 A1    Sep. 22, 2011

Related U.S. Application Data

(63) Continuation of application No. 12/509,604, filed on Jul. 27, 2009, now Pat. No. 7,951,189, which is a continuation of application No. 11/232,403, filed on Sep. 21, 2005, now Pat. No. 7,569,071.

(51) Int. Cl.
*A61F 2/06* (2006.01)

(52) U.S. Cl.
USPC ......... 623/1.24; 623/1.26; 623/2.1; 623/2.14; 623/2.17; 623/2.18

(58) Field of Classification Search
USPC ............. 623/1.24, 1.26, 2.1, 2.11, 2.12–2.19, 623/2.38–2.41
See application file for complete search history.

(56) References Cited

U.S. PATENT DOCUMENTS

| | | |
|---|---|---|
| 3,671,979 A | 6/1972 | Moulopoulos |
| 4,291,420 A | 9/1981 | Reul |
| 4,787,901 A | 11/1988 | Baykut |
| 4,872,874 A | 10/1989 | Taheri |
| 4,935,030 A | 6/1990 | Alonso |
| 4,994,077 A | 2/1991 | Dobben |
| 5,002,567 A | 3/1991 | Bona |
| 5,141,491 A | 8/1992 | Bowald |
| 5,163,953 A | 11/1992 | Vince |
| 5,219,355 A | 6/1993 | Parodi |
| 5,254,127 A | 10/1993 | Wholey |
| 5,327,774 A | 7/1994 | Nguyen |
| 5,332,402 A | 7/1994 | Teitelbaum |
| 5,370,685 A | 12/1994 | Stevens |
| 5,411,552 A | 5/1995 | Andersen |
| 5,469,868 A | 11/1995 | Reger |
| 5,480,423 A | 1/1996 | Ravenscroft |
| 5,500,014 A | 3/1996 | Quijano |
| 5,545,214 A | 8/1996 | Stevens |
| 5,554,185 A | 9/1996 | Block |
| 5,643,208 A | 7/1997 | Parodi |

(Continued)

FOREIGN PATENT DOCUMENTS

| EP | 0380666 | 8/1990 |
|---|---|---|
| EP | 0466518 | 1/1992 |

(Continued)

*Primary Examiner* — David Isabella
*Assistant Examiner* — Suba Ganesan
(74) *Attorney, Agent, or Firm* — Vidas, Arrett & Steinkraus, P.A.

(57) ABSTRACT

A valve with a frame and valve leaflets that provide a sinus pocket. The valve provides for unidirectional flow of a liquid through the valve.

10 Claims, 13 Drawing Sheets

U.S. PATENT DOCUMENTS

| | | | |
|---|---|---|---|
| 5,693,087 | A | 12/1997 | Parodi |
| 5,713,953 | A | 2/1998 | Vallana |
| 5,716,370 | A | 2/1998 | Williamson, IV |
| 5,735,859 | A | 4/1998 | Fischell |
| 5,741,326 | A | 4/1998 | Solovay |
| 5,741,333 | A | 4/1998 | Frid |
| 5,800,506 | A | 9/1998 | Perouse |
| 5,824,061 | A | 10/1998 | Quijano |
| 5,879,320 | A | 3/1999 | Cazenave |
| 5,895,419 | A | 4/1999 | Tweden |
| 5,910,170 | A | 6/1999 | Reimink |
| 6,010,531 | A | 1/2000 | Donlon |
| 6,042,607 | A | 3/2000 | Williamson, IV |
| 6,139,575 | A | 10/2000 | Shu |
| 6,287,334 | B1 | 9/2001 | Moll |
| 6,312,447 | B1 | 11/2001 | Grimes |
| 6,355,030 | B1 | 3/2002 | Aldrich |
| 6,402,780 | B2 | 6/2002 | Williamson, IV |
| 6,419,696 | B1 | 7/2002 | Ortiz |
| 6,425,916 | B1 | 7/2002 | Garrison |
| 6,440,164 | B1 | 8/2002 | DiMatteo |
| 6,451,054 | B1 | 9/2002 | Stevens |
| 6,454,799 | B1 | 9/2002 | Schreck |
| 6,461,366 | B1 | 10/2002 | Seguin |
| 6,503,272 | B2 | 1/2003 | Duerig |
| 6,508,833 | B2 | 1/2003 | Pavcnik |
| 6,564,805 | B2 | 5/2003 | Garrison |
| 6,569,196 | B1 | 5/2003 | Vesely |
| 6,602,286 | B1 | 8/2003 | Strecker |
| 6,629,534 | B1 | 10/2003 | St. Goar et al. |
| 6,635,085 | B1 | 10/2003 | Caffey |
| 6,666,885 | B2 | 12/2003 | Moe |
| 6,666,886 | B1 | 12/2003 | Tranquillo |
| 6,669,725 | B2 | 12/2003 | Scott |
| 6,673,109 | B2 | 1/2004 | Cox |
| 6,676,698 | B2 | 1/2004 | McGuckin, Jr. |
| 6,676,702 | B2 | 1/2004 | Mathis |
| 6,682,558 | B2 | 1/2004 | Tu |
| 6,682,559 | B2 | 1/2004 | Myers |
| 6,685,739 | B2 | 2/2004 | DiMatteo |
| 6,692,512 | B2 | 2/2004 | Jang |
| 6,695,866 | B1 | 2/2004 | Kuehn |
| 6,695,878 | B2 | 2/2004 | McGuckin |
| 6,709,456 | B2 | 3/2004 | Langberg |
| 6,709,457 | B1 | 3/2004 | Otte |
| 6,716,241 | B2 | 4/2004 | Wilder |
| 6,716,244 | B2 | 4/2004 | Klaco |
| 6,719,767 | B1 | 4/2004 | Kimblad |
| 6,719,784 | B2 | 4/2004 | Henderson |
| 6,719,786 | B2 | 4/2004 | Ryan |
| 6,719,787 | B2 | 4/2004 | Cox |
| 6,719,788 | B2 | 4/2004 | Cox |
| 6,719,789 | B2 | 4/2004 | Cox |
| 6,719,790 | B2 | 4/2004 | Brendzel |
| 6,723,038 | B1 | 4/2004 | Schroeder |
| 6,723,122 | B2 | 4/2004 | Yang |
| 6,723,123 | B1 | 4/2004 | Kazatchkov |
| 6,726,715 | B2 | 4/2004 | Sutherland |
| 6,726,716 | B2 | 4/2004 | Marquez |
| 6,726,717 | B2 | 4/2004 | Alfieri |
| 6,730,118 | B2 | 5/2004 | Spenser |
| 6,730,121 | B2 | 5/2004 | Ortiz |
| 6,730,122 | B1 | 5/2004 | Pan |
| 6,736,845 | B2 | 5/2004 | Marquez |
| 6,736,846 | B2 | 5/2004 | Cox |
| 6,749,630 | B2 | 6/2004 | McCarthy |
| 6,752,813 | B2 | 6/2004 | Goldfarb |
| 6,752,828 | B2 | 6/2004 | Thornton |
| 6,755,857 | B2 | 6/2004 | Peterson |
| 6,761,734 | B2 | 7/2004 | Suhr |
| 6,761,735 | B2 | 7/2004 | Eberhardt |
| 6,764,494 | B2 | 7/2004 | Menz |
| 6,764,508 | B1 | 7/2004 | Roehe |
| 6,764,509 | B2 | 7/2004 | Chinn |
| 6,764,510 | B2 | 7/2004 | Vidlund |
| 6,767,362 | B2 | 7/2004 | Schreck |
| 6,769,434 | B2 | 8/2004 | Liddicoat |
| 6,770,083 | B2 | 8/2004 | Seguin |
| 6,780,200 | B2 | 8/2004 | Jansen |
| 6,786,924 | B2 | 9/2004 | Ryan |
| 6,786,925 | B1 | 9/2004 | Schoon et al. |
| 6,790,229 | B1 | 9/2004 | Berreklouw |
| 6,790,230 | B2 | 9/2004 | Beyersdorf |
| 6,790,231 | B2 | 9/2004 | Liddicoat |
| 6,793,673 | B2 | 9/2004 | Kowalsky |
| 6,797,000 | B2 | 9/2004 | Simpson |
| 6,797,001 | B2 | 9/2004 | Mathis |
| 6,797,002 | B2 | 9/2004 | Spence |
| 6,802,860 | B2 | 10/2004 | Cosgrove |
| 6,805,710 | B2 | 10/2004 | Bolling |
| 6,805,711 | B2 | 10/2004 | Quijano |
| 6,810,882 | B2 | 11/2004 | Langberg |
| 6,821,297 | B2 | 11/2004 | Snyders |
| 6,824,562 | B2 | 11/2004 | Mathis |
| 6,830,584 | B1 | 12/2004 | Seguin |
| 6,830,585 | B1 | 12/2004 | Artof |
| 6,837,902 | B2 | 1/2005 | Nguyen |
| 6,840,246 | B2 | 1/2005 | Downing |
| 6,840,957 | B2 | 1/2005 | DiMatteo |
| 6,846,324 | B2 | 1/2005 | Stobie |
| 6,846,325 | B2 | 1/2005 | Liddicoat |
| 6,858,039 | B2 | 2/2005 | McCarthy |
| 6,869,444 | B2 | 3/2005 | Gabbay |
| 6,872,226 | B2 | 3/2005 | Cali |
| 6,875,224 | B2 | 4/2005 | Grimes |
| 6,875,230 | B1 | 4/2005 | Morita |
| 6,875,231 | B2 | 4/2005 | Anduiza |
| 6,881,199 | B2 | 4/2005 | Wilk |
| 6,881,224 | B2 | 4/2005 | Kruse |
| 6,883,522 | B2 | 4/2005 | Spence |
| 6,890,352 | B1 | 5/2005 | Lentell |
| 6,890,353 | B2 | 5/2005 | Cohn |
| 6,893,459 | B1 | 5/2005 | Macoviak |
| 6,893,460 | B2 | 5/2005 | Spenser |
| 6,896,700 | B2 | 5/2005 | Lu |
| 6,902,576 | B2 | 6/2005 | Drasler |
| 6,908,478 | B2 | 6/2005 | Alferness |
| 6,908,481 | B2 | 6/2005 | Cribier |
| 6,911,043 | B2 | 6/2005 | Myers |
| 6,913,608 | B2 | 7/2005 | Liddicoat |
| 6,916,338 | B2 | 7/2005 | Speziali |
| 6,918,917 | B1 | 7/2005 | Nguyen |
| 6,921,407 | B2 | 7/2005 | Nguyen |
| 6,921,811 | B2 | 7/2005 | Zamora |
| 6,926,715 | B1 | 8/2005 | Hauck |
| 6,926,730 | B1 | 8/2005 | Nguyen |
| 6,929,653 | B2 | 8/2005 | Strecter |
| 6,932,838 | B2 | 8/2005 | Schwartz |
| 6,936,067 | B2 | 8/2005 | Buchanan |
| 6,939,359 | B2 | 9/2005 | Tu |
| 6,942,694 | B2 | 9/2005 | Liddicoat |
| 6,945,957 | B2 | 9/2005 | Freyman |
| 6,945,978 | B1 | 9/2005 | Hyde |
| 6,945,996 | B2 | 9/2005 | Sedransk |
| 6,945,997 | B2 | 9/2005 | Huynh |
| 6,949,122 | B2 | 9/2005 | Adams |
| 6,951,571 | B1 | 10/2005 | Srivastava |
| 6,951,573 | B1 | 10/2005 | Dilling |
| 6,953,332 | B1 | 10/2005 | Kurk |
| 6,955,689 | B2 | 10/2005 | Ryan |
| 6,958,076 | B2 | 10/2005 | Acosta |
| 6,962,605 | B2 | 11/2005 | Cosgrove |
| 6,964,682 | B2 | 11/2005 | Nguyen-Thien-Nhon |
| 6,964,683 | B2 | 11/2005 | Kowalsky |
| 6,964,684 | B2 | 11/2005 | Ortiz |
| 6,966,925 | B2 | 11/2005 | Stobie |
| 6,966,926 | B2 | 11/2005 | Mathis |
| 6,974,464 | B2 | 12/2005 | Quijano |
| 6,974,474 | B2 | 12/2005 | Pavcnik |
| 6,974,476 | B2 | 12/2005 | McGuckin |
| 6,976,995 | B2 | 12/2005 | Mathis |
| 6,979,350 | B2 | 12/2005 | Moll |
| 6,986,775 | B2 | 1/2006 | Morales |
| 6,989,027 | B2 | 1/2006 | Allen |
| 6,989,028 | B2 | 1/2006 | Lashinski |
| 6,997,950 | B2 | 2/2006 | Chawla |
| 6,997,951 | B2 | 2/2006 | Solem |

| Patent No. | Date | Name |
|---|---|---|
| 7,004,176 B2 | 2/2006 | Lau |
| 7,007,396 B2 | 3/2006 | Rudko |
| 7,011,669 B2 | 3/2006 | Kimblad |
| 7,011,681 B2 | 3/2006 | Vesely |
| 7,011,682 B2 | 3/2006 | Lashinski |
| 7,018,406 B2 | 3/2006 | Seguin |
| 7,018,407 B1 | 3/2006 | Wright |
| 7,018,408 B2 | 3/2006 | Bailey |
| 7,022,134 B1 | 4/2006 | Quijano |
| 7,025,780 B2 | 4/2006 | Gabbay |
| 7,033,390 B2 | 4/2006 | Johnson |
| 7,037,333 B2 | 5/2006 | Myers |
| 7,037,334 B1 | 5/2006 | Hlavka |
| 7,041,128 B2 | 5/2006 | McGuckin, Jr. |
| 7,041,132 B2 | 5/2006 | Quijano |
| 7,044,966 B2 | 5/2006 | Svanidze |
| 7,044,967 B1 | 5/2006 | Solem |
| 7,048,754 B2 | 5/2006 | Martin |
| 7,048,757 B2 | 5/2006 | Shaknovich |
| 7,052,487 B2 | 5/2006 | Cohn |
| 7,052,507 B2 | 5/2006 | Wakuda |
| 7,063,722 B2 | 6/2006 | Marquez |
| 7,066,954 B2 | 6/2006 | Ryan |
| 7,070,616 B2 | 7/2006 | Majercak |
| 7,070,618 B2 | 7/2006 | Streeter |
| 7,077,862 B2 | 7/2006 | Vidlund |
| 7,081,131 B2 | 7/2006 | Thornton |
| 7,087,064 B1 | 8/2006 | Hyde |
| 7,089,051 B2 | 8/2006 | Javerud |
| 7,090,695 B2 | 8/2006 | Solem |
| 7,967,853 B2 | 6/2011 | Eidenschink |
| 2001/0011187 A1 | 8/2001 | Pavcnik |
| 2002/0013571 A1 | 1/2002 | Goldfarb |
| 2002/0026216 A1 | 2/2002 | Grimes |
| 2002/0082630 A1 | 6/2002 | Menz |
| 2002/0123802 A1 | 9/2002 | Snyders |
| 2002/0151970 A1 | 10/2002 | Garrison |
| 2002/0178570 A1 | 12/2002 | Sogard |
| 2002/0183835 A1 | 12/2002 | Taylor |
| 2002/0183838 A1 | 12/2002 | Liddicoat |
| 2002/0198594 A1 | 12/2002 | Schreck |
| 2003/0050694 A1 | 3/2003 | Yang |
| 2003/0130729 A1 | 7/2003 | Paniagua |
| 2003/0163194 A1 | 8/2003 | Quijano |
| 2003/0167071 A1 | 9/2003 | Martin |
| 2003/0171806 A1 | 9/2003 | Mathis |
| 2003/0199975 A1 | 10/2003 | Gabbay |
| 2003/0229394 A1 | 12/2003 | Ogle |
| 2003/0229395 A1 | 12/2003 | Cox |
| 2003/0233142 A1 | 12/2003 | Morales |
| 2003/0236568 A1 | 12/2003 | Hojeibane |
| 2003/0236569 A1 | 12/2003 | Mathis |
| 2004/0002719 A1 | 1/2004 | Oz |
| 2004/0003819 A1 | 1/2004 | St. Goar |
| 2004/0010305 A1 | 1/2004 | Alferness |
| 2004/0015230 A1 | 1/2004 | Moll |
| 2004/0015232 A1 | 1/2004 | Shu |
| 2004/0015233 A1 | 1/2004 | Jansen |
| 2004/0019374 A1 | 1/2004 | Hojeibane |
| 2004/0019377 A1 | 1/2004 | Taylor |
| 2004/0019378 A1 | 1/2004 | Hlavka |
| 2004/0024447 A1 | 2/2004 | Haverich |
| 2004/0024451 A1 | 2/2004 | Johnson |
| 2004/0024452 A1 | 2/2004 | Kruse |
| 2004/0030321 A1 | 2/2004 | Fangrow |
| 2004/0030381 A1 | 2/2004 | Shu |
| 2004/0030382 A1 | 2/2004 | St. Goar |
| 2004/0030405 A1 | 2/2004 | Carpentier |
| 2004/0034380 A1 | 2/2004 | Woolfson |
| 2004/0034411 A1 | 2/2004 | Quijano |
| 2004/0039436 A1 | 2/2004 | Spenser |
| 2004/0039442 A1 | 2/2004 | St. Goar |
| 2004/0039443 A1 | 2/2004 | Solem |
| 2004/0044350 A1 | 3/2004 | Martin |
| 2004/0044365 A1 | 3/2004 | Bachman |
| 2004/0044403 A1 | 3/2004 | Bischoff |
| 2004/0049207 A1 | 3/2004 | Goldfarb |
| 2004/0049211 A1 | 3/2004 | Tremulis |
| 2004/0049266 A1 | 3/2004 | Anduiza |
| 2004/0059351 A1 | 3/2004 | Eigler |
| 2004/0059411 A1 | 3/2004 | Strecker |
| 2004/0059412 A1 | 3/2004 | Lytle, IV |
| 2004/0060161 A1 | 4/2004 | Leal |
| 2004/0073301 A1 | 4/2004 | Donlon |
| 2004/0073302 A1 | 4/2004 | Rourke |
| 2004/0078072 A1 | 4/2004 | Tu |
| 2004/0078074 A1 | 4/2004 | Anderson |
| 2004/0082910 A1 | 4/2004 | Constantz |
| 2004/0082923 A1 | 4/2004 | Field |
| 2004/0082991 A1 | 4/2004 | Nguyen |
| 2004/0087975 A1 | 5/2004 | Lucatero |
| 2004/0088045 A1 | 5/2004 | Cox |
| 2004/0088046 A1 | 5/2004 | Speziali |
| 2004/0092858 A1 | 5/2004 | Wilson |
| 2004/0093060 A1 | 5/2004 | Seguin |
| 2004/0093070 A1 | 5/2004 | Hojeibane |
| 2004/0093080 A1 | 5/2004 | Helmus |
| 2004/0097979 A1 | 5/2004 | Svanidze |
| 2004/0098098 A1 | 5/2004 | McGuckin, Jr. |
| 2004/0098112 A1 | 5/2004 | DiMatteo |
| 2004/0102839 A1 | 5/2004 | Cohn |
| 2004/0102840 A1 | 5/2004 | Solem |
| 2004/0102842 A1 | 5/2004 | Jansen |
| 2004/0106976 A1 | 6/2004 | Bailey |
| 2004/0106990 A1 | 6/2004 | Spence |
| 2004/0106991 A1 | 6/2004 | Hopkins |
| 2004/0111096 A1 | 6/2004 | Tu |
| 2004/0117009 A1 | 6/2004 | Cali |
| 2004/0122448 A1 | 6/2004 | Levine |
| 2004/0122512 A1 | 6/2004 | Navia |
| 2004/0122513 A1 | 6/2004 | Navia |
| 2004/0122514 A1 | 6/2004 | Fogarty |
| 2004/0122515 A1 | 6/2004 | Chu |
| 2004/0122516 A1 | 6/2004 | Fogarty |
| 2004/0127979 A1 | 7/2004 | Wilson |
| 2004/0127980 A1 | 7/2004 | Kowalsky |
| 2004/0127981 A1 | 7/2004 | Randert |
| 2004/0127982 A1 | 7/2004 | Machold |
| 2004/0133220 A1 | 7/2004 | Lashinski |
| 2004/0133267 A1 | 7/2004 | Lane |
| 2004/0133273 A1 | 7/2004 | Cox |
| 2004/0138742 A1 | 7/2004 | Myers |
| 2004/0138743 A1 | 7/2004 | Myers |
| 2004/0138744 A1 | 7/2004 | Lashinski |
| 2004/0138745 A1 | 7/2004 | Macoviak |
| 2004/0148018 A1 | 7/2004 | Carpentier |
| 2004/0148019 A1 | 7/2004 | Vidlund |
| 2004/0148020 A1 | 7/2004 | Vidlund |
| 2004/0153052 A1 | 8/2004 | Mathis |
| 2004/0153146 A1 | 8/2004 | Lashinski |
| 2004/0153147 A1 | 8/2004 | Mathis |
| 2004/0158321 A1 | 8/2004 | Reuter |
| 2004/0162610 A1 | 8/2004 | Liska |
| 2004/0167539 A1 | 8/2004 | Keuhn |
| 2004/0167619 A1 | 8/2004 | Case |
| 2004/0167620 A1 | 8/2004 | Ortiz |
| 2004/0172046 A1 | 9/2004 | Hlavka |
| 2004/0176839 A1 | 9/2004 | Huynh |
| 2004/0176840 A1 | 9/2004 | Langberg |
| 2004/0181238 A1 | 9/2004 | Zarbatany |
| 2004/0186444 A1 | 9/2004 | Daly |
| 2004/0186558 A1 | 9/2004 | Pavcnik |
| 2004/0186561 A1 | 9/2004 | Mcguckin |
| 2004/0186563 A1 | 9/2004 | Lobbi |
| 2004/0186565 A1 | 9/2004 | Schreck |
| 2004/0186566 A1 | 9/2004 | Hindrichs |
| 2004/0193191 A1 | 9/2004 | Starksen |
| 2004/0193253 A1 | 9/2004 | Thorpe |
| 2004/0193260 A1 | 9/2004 | Alferness |
| 2004/0199155 A1 | 10/2004 | Mollenauer |
| 2004/0199183 A1 | 10/2004 | Oz |
| 2004/0199191 A1 | 10/2004 | Schwartz |
| 2004/0204758 A1 | 10/2004 | Eberhardt |
| 2004/0206363 A1 | 10/2004 | Mccarthy |
| 2004/0210240 A1 | 10/2004 | Saint |
| 2004/0210301 A1 | 10/2004 | Obermiller |
| 2004/0210303 A1 | 10/2004 | Sedransk |
| 2004/0210304 A1 | 10/2004 | Seguin |

| | | | | | | |
|---|---|---|---|---|---|---|
| 2004/0210305 A1 | 10/2004 | Shu | | 2005/0075724 A1 | 4/2005 | Svanidze |
| 2004/0210306 A1 | 10/2004 | Quijano | | 2005/0075725 A1 | 4/2005 | Rowe |
| 2004/0210307 A1 | 10/2004 | Khairkhahan | | 2005/0075726 A1 | 4/2005 | Svanidze |
| 2004/0215333 A1 | 10/2004 | Duran | | 2005/0075728 A1 | 4/2005 | Nguyen |
| 2004/0215339 A1 | 10/2004 | Drasler | | 2005/0075729 A1 | 4/2005 | Nguyen |
| 2004/0220654 A1 | 11/2004 | Mathis | | 2005/0075730 A1 | 4/2005 | Myers |
| 2004/0220657 A1 | 11/2004 | Nieminen | | 2005/0075731 A1 | 4/2005 | Artof |
| 2004/0225322 A1 | 11/2004 | Garrison | | 2005/0080483 A1 | 4/2005 | Solem |
| 2004/0225344 A1 | 11/2004 | Hoffa | | 2005/0085900 A1 | 4/2005 | Case |
| 2004/0225348 A1 | 11/2004 | Case | | 2005/0085903 A1 | 4/2005 | Lau |
| 2004/0225352 A1 | 11/2004 | Osborne | | 2005/0085904 A1 | 4/2005 | Lemmon |
| 2004/0225353 A1 | 11/2004 | McGuckin, Jr. | | 2005/0090846 A1 | 4/2005 | Pedersen |
| 2004/0225354 A1 | 11/2004 | Allen | | 2005/0096735 A1 | 5/2005 | Hojeibane |
| 2004/0225355 A1 | 11/2004 | Stevens | | 2005/0096738 A1 | 5/2005 | Cali |
| 2004/0225356 A1 | 11/2004 | Frater | | 2005/0096739 A1 | 5/2005 | Cao |
| 2004/0230117 A1 | 11/2004 | Tosaya | | 2005/0096740 A1 | 5/2005 | Langberg |
| 2004/0230297 A1 | 11/2004 | Thornton | | 2005/0101975 A1 | 5/2005 | Nguyen |
| 2004/0236411 A1 | 11/2004 | Sarac | | 2005/0102026 A1 | 5/2005 | Turner |
| 2004/0236418 A1 | 11/2004 | Stevens | | 2005/0107810 A1 | 5/2005 | Morales |
| 2004/0236419 A1 | 11/2004 | Milo | | 2005/0107811 A1 | 5/2005 | Starksen |
| 2004/0243153 A1 | 12/2004 | Liddicoat | | 2005/0107812 A1 | 5/2005 | Starksen |
| 2004/0243219 A1 | 12/2004 | Fischer | | 2005/0107872 A1 | 5/2005 | Mensah |
| 2004/0243227 A1 | 12/2004 | Starksen | | 2005/0113910 A1 | 5/2005 | Paniagua |
| 2004/0243228 A1 | 12/2004 | Kowalsky | | 2005/0119673 A1 | 6/2005 | Gordon |
| 2004/0243230 A1 | 12/2004 | Navia | | 2005/0119734 A1 | 6/2005 | Spence |
| 2004/0254600 A1 | 12/2004 | Zarbatany | | 2005/0119735 A1 | 6/2005 | Spence |
| 2004/0254636 A1 | 12/2004 | Flagle | | 2005/0125011 A1 | 6/2005 | Spence |
| 2004/0260276 A1 | 12/2004 | Rudko | | 2005/0131438 A1 | 6/2005 | Cohn |
| 2004/0260317 A1 | 12/2004 | Bloom | | 2005/0137449 A1 | 6/2005 | Nieminen |
| 2004/0260322 A1 | 12/2004 | Rudko | | 2005/0137450 A1 | 6/2005 | Aronson |
| 2004/0260389 A1 | 12/2004 | Case | | 2005/0137451 A1 | 6/2005 | Gordon |
| 2004/0260390 A1 | 12/2004 | Sarac | | 2005/0137676 A1 | 6/2005 | Richardson |
| 2004/0260393 A1 | 12/2004 | Randert | | 2005/0137681 A1 | 6/2005 | Shoemaker |
| 2004/0260394 A1 | 12/2004 | Douk | | 2005/0137682 A1 | 6/2005 | Justin |
| 2004/0267357 A1 | 12/2004 | Allen | | 2005/0137685 A1 | 6/2005 | Nieminen |
| 2005/0004583 A1 | 1/2005 | Oz | | 2005/0137686 A1 | 6/2005 | Salahieh |
| 2005/0004667 A1 | 1/2005 | Swinford | | 2005/0137688 A1 | 6/2005 | Salahieh |
| 2005/0010285 A1 | 1/2005 | Lambrecht | | 2005/0137689 A1 | 6/2005 | Salahieh |
| 2005/0010287 A1 | 1/2005 | Macoviak | | 2005/0137690 A1 | 6/2005 | Salahieh |
| 2005/0015112 A1 | 1/2005 | Cohn | | 2005/0137691 A1 | 6/2005 | Salahieh |
| 2005/0021056 A1 | 1/2005 | St. Goar | | 2005/0137692 A1 | 6/2005 | Haug |
| 2005/0021136 A1 | 1/2005 | Xie | | 2005/0137693 A1 | 6/2005 | Haug |
| 2005/0027261 A1 | 2/2005 | Weaver | | 2005/0137694 A1 | 6/2005 | Haug |
| 2005/0027348 A1 | 2/2005 | Case | | 2005/0137696 A1 | 6/2005 | Salahieh |
| 2005/0027351 A1 | 2/2005 | Reuter | | 2005/0137697 A1 | 6/2005 | Salahieh |
| 2005/0027353 A1 | 2/2005 | Alferness | | 2005/0137698 A1 | 6/2005 | Salahieh |
| 2005/0033398 A1 | 2/2005 | Seguin | | 2005/0137699 A1 | 6/2005 | Salahieh |
| 2005/0033419 A1 | 2/2005 | Alferness | | 2005/0137700 A1 | 6/2005 | Spence |
| 2005/0033446 A1 | 2/2005 | Deem | | 2005/0137701 A1 | 6/2005 | Salahieh |
| 2005/0038506 A1 | 2/2005 | Webler | | 2005/0137702 A1 | 6/2005 | Haug |
| 2005/0038507 A1 | 2/2005 | Alferness | | 2005/0143807 A1 | 6/2005 | Pavcnik |
| 2005/0043790 A1 | 2/2005 | Seguin | | 2005/0143809 A1 | 6/2005 | Salahieh |
| 2005/0043792 A1 | 2/2005 | Solem | | 2005/0143810 A1 | 6/2005 | Dauner |
| 2005/0049679 A1 | 3/2005 | Taylor | | 2005/0143811 A1 | 6/2005 | Realyvasquez |
| 2005/0049692 A1 | 3/2005 | Numamoto | | 2005/0149014 A1 | 7/2005 | Hauck |
| 2005/0049696 A1 | 3/2005 | Siess | | 2005/0149179 A1 | 7/2005 | Mathis |
| 2005/0049697 A1 | 3/2005 | Sievers | | 2005/0149180 A1 | 7/2005 | Mathis |
| 2005/0054977 A1 | 3/2005 | Laird | | 2005/0149181 A1 | 7/2005 | Eberhardt |
| 2005/0055079 A1 | 3/2005 | Duran | | 2005/0159810 A1 | 7/2005 | Filsoufi |
| 2005/0055087 A1 | 3/2005 | Starksen | | 2005/0159811 A1 | 7/2005 | Lane |
| 2005/0055088 A1 | 3/2005 | Liddicoat | | 2005/0165477 A1 | 7/2005 | Anduiza |
| 2005/0055089 A1 | 3/2005 | Macoviak | | 2005/0165478 A1 | 7/2005 | Song |
| 2005/0060029 A1 | 3/2005 | Le | | 2005/0171472 A1 | 8/2005 | Lutter |
| 2005/0060030 A1 | 3/2005 | Lashinski | | 2005/0171601 A1 | 8/2005 | Cosgrove |
| 2005/0065460 A1 | 3/2005 | Laird | | 2005/0177227 A1 | 8/2005 | Heim |
| 2005/0065550 A1 | 3/2005 | Starksen | | 2005/0177228 A1 | 8/2005 | Solem |
| 2005/0065594 A1 | 3/2005 | Dimatteo | | 2005/0182483 A1 | 8/2005 | Osborne |
| 2005/0065597 A1 | 3/2005 | Lansac | | 2005/0184122 A1 | 8/2005 | Hlavka |
| 2005/0070998 A1 | 3/2005 | Rourke | | 2005/0187614 A1 | 8/2005 | Agnew |
| 2005/0075584 A1 | 4/2005 | Cali | | 2005/0187616 A1 | 8/2005 | Realyvasquez |
| 2005/0075659 A1 | 4/2005 | Realyvasquez | | 2005/0187617 A1 | 8/2005 | Navia |
| 2005/0075662 A1 | 4/2005 | Pedersen | | 2005/0192606 A1 | 9/2005 | Paul |
| 2005/0075712 A1 | 4/2005 | Biancucci | | 2005/0192665 A1 | 9/2005 | Spenser |
| 2005/0075713 A1 | 4/2005 | Biancucci | | 2005/0197692 A1 | 9/2005 | Pai |
| 2005/0075717 A1 | 4/2005 | Nguyen | | 2005/0197693 A1 | 9/2005 | Pai |
| 2005/0075718 A1 | 4/2005 | Nguyen | | 2005/0197694 A1 | 9/2005 | Pai |
| 2005/0075719 A1 | 4/2005 | Bergheim | | 2005/0203549 A1 | 9/2005 | Realyvasquez |
| 2005/0075720 A1 | 4/2005 | Nguyen | | 2005/0203605 A1 | 9/2005 | Dolan |
| 2005/0075723 A1 | 4/2005 | Schroeder | | 2005/0203614 A1 | 9/2005 | Forster |

| Publication No. | Date | Name |
|---|---|---|
| 2005/0203615 A1 | 9/2005 | Forster |
| 2005/0203616 A1 | 9/2005 | Cribier |
| 2005/0203617 A1 | 9/2005 | Forster |
| 2005/0203618 A1 | 9/2005 | Sharkawy |
| 2005/0216039 A1 | 9/2005 | Lederman |
| 2005/0216077 A1 | 9/2005 | Mathis |
| 2005/0216078 A1 | 9/2005 | Starksen |
| 2005/0222675 A1 | 10/2005 | Sauter |
| 2005/0222678 A1 | 10/2005 | Lashinski |
| 2005/0228422 A1 | 10/2005 | Machold |
| 2005/0228479 A1 | 10/2005 | Pavcnik |
| 2005/0228486 A1 | 10/2005 | Case |
| 2005/0228494 A1 | 10/2005 | Marquez |
| 2005/0228495 A1 | 10/2005 | Macoviak |
| 2005/0228496 A1 | 10/2005 | Mensah |
| 2005/0234541 A1 | 10/2005 | Hunt |
| 2005/0234546 A1 | 10/2005 | Nugent |
| 2005/0240200 A1 | 10/2005 | Bergheim |
| 2005/0240202 A1 | 10/2005 | Shennib |
| 2005/0240255 A1 | 10/2005 | Schaeffer |
| 2005/0240259 A1 | 10/2005 | Sisken |
| 2005/0240262 A1 | 10/2005 | White |
| 2005/0244460 A1 | 11/2005 | Alferiev |
| 2005/0246013 A1 | 11/2005 | Gabbay |
| 2005/0251251 A1 | 11/2005 | Cribier |
| 2005/0256566 A1 | 11/2005 | Gabbay |
| 2005/0261704 A1 | 11/2005 | Mathis |
| 2005/0261759 A1 | 11/2005 | Lambrecht |
| 2005/0267493 A1 | 12/2005 | Schreck |
| 2005/0267560 A1 | 12/2005 | Bates |
| 2005/0267565 A1 | 12/2005 | Dave |
| 2005/0267571 A1 | 12/2005 | Spence |
| 2005/0267573 A9 | 12/2005 | Macoviak |
| 2005/0267574 A1 | 12/2005 | Cohn |
| 2005/0272969 A1 | 12/2005 | Alferness |
| 2005/0273160 A1 | 12/2005 | Lashinski |
| 2005/0278015 A1 | 12/2005 | Dave |
| 2005/0283178 A1 | 12/2005 | Flagle |
| 2005/0288779 A1 | 12/2005 | Shaoulian |
| 2006/0000715 A1 | 1/2006 | Whitcher |
| 2006/0004439 A1 | 1/2006 | Spenser |
| 2006/0004442 A1 | 1/2006 | Spenser |
| 2006/0009804 A1 | 1/2006 | Pederson |
| 2006/0009841 A1 | 1/2006 | Mcguckin |
| 2006/0009842 A1 | 1/2006 | Huynh |
| 2006/0013805 A1 | 1/2006 | Hebbel |
| 2006/0013855 A1 | 1/2006 | Carpenter |
| 2006/0015136 A1 | 1/2006 | Besselink |
| 2006/0015178 A1 | 1/2006 | Moaddeb |
| 2006/0015179 A1 | 1/2006 | Bulman-Fleming |
| 2006/0020275 A1 | 1/2006 | Goldfarb |
| 2006/0020327 A1 | 1/2006 | Lashinski |
| 2006/0020332 A1 | 1/2006 | Lashinski |
| 2006/0020334 A1 | 1/2006 | Lashinski |
| 2006/0020335 A1 | 1/2006 | Kowalsky |
| 2006/0020336 A1 | 1/2006 | Liddicoat |
| 2006/0025750 A1 | 2/2006 | Starksen |
| 2006/0025784 A1 | 2/2006 | Starksen |
| 2006/0025787 A1 | 2/2006 | Morales |
| 2006/0025854 A1 | 2/2006 | Lashinski |
| 2006/0025855 A1 | 2/2006 | Lashinski |
| 2006/0025856 A1 | 2/2006 | Ryan |
| 2006/0025857 A1 | 2/2006 | Bergheim |
| 2006/0030747 A1 | 2/2006 | Kantrowitz |
| 2006/0030866 A1 | 2/2006 | Schreck |
| 2006/0030882 A1 | 2/2006 | Adams |
| 2006/0030885 A1 | 2/2006 | Hyde |
| 2006/0036317 A1 | 2/2006 | Vidlund |
| 2006/0041305 A1 | 2/2006 | Lauterjung |
| 2006/0041306 A1 | 2/2006 | Vidlund |
| 2006/0047297 A1 | 3/2006 | Case |
| 2006/0047338 A1 | 3/2006 | Jenson |
| 2006/0047343 A1 | 3/2006 | Oviatt |
| 2006/0052804 A1 | 3/2006 | Mialhe |
| 2006/0052867 A1 | 3/2006 | Revuelta |
| 2006/0058817 A1 | 3/2006 | Starksen |
| 2006/0058865 A1 | 3/2006 | Case |
| 2006/0058871 A1 | 3/2006 | Zakay |
| 2006/0058889 A1 | 3/2006 | Case |
| 2006/0064115 A1 | 3/2006 | Allen |
| 2006/0064116 A1 | 3/2006 | Allen |
| 2006/0064118 A1 | 3/2006 | Kimblad |
| 2006/0064174 A1 | 3/2006 | Zadno |
| 2006/0069400 A1 | 3/2006 | Burnett |
| 2006/0069429 A1 | 3/2006 | Spence |
| 2006/0069430 A9 | 3/2006 | Rahdert |
| 2006/0074483 A1 | 4/2006 | Schrayer |
| 2006/0074484 A1 | 4/2006 | Huber |
| 2006/0074485 A1 | 4/2006 | Realyvasquez |
| 2006/0085060 A1 | 4/2006 | Campbell |
| 2006/0089708 A1 | 4/2006 | Osse |
| 2006/0095115 A1 | 5/2006 | Bladillah |
| 2006/0095125 A1 | 5/2006 | Chinn |
| 2006/0099326 A1 | 5/2006 | Keogh |
| 2006/0100697 A1 | 5/2006 | Casanova |
| 2006/0100699 A1 | 5/2006 | Vidlund |
| 2006/0106278 A1 | 5/2006 | Machold |
| 2006/0106279 A1 | 5/2006 | Machold |
| 2006/0106456 A9 | 5/2006 | Machold |
| 2006/0111660 A1 | 5/2006 | Wolf |
| 2006/0111773 A1 | 5/2006 | Rittgers |
| 2006/0111774 A1 | 5/2006 | Samkov |
| 2006/0116572 A1 | 6/2006 | Case |
| 2006/0116756 A1 | 6/2006 | Solem |
| 2006/0122686 A1 | 6/2006 | Gilad |
| 2006/0122692 A1 | 6/2006 | Gilad |
| 2006/0122693 A1 | 6/2006 | Biadillah |
| 2006/0127443 A1 | 6/2006 | Helmus |
| 2006/0129235 A1 | 6/2006 | Seguin |
| 2006/0129236 A1 | 6/2006 | McCarthy |
| 2006/0135476 A1 | 6/2006 | Kutryk |
| 2006/0135964 A1 | 6/2006 | Vesely |
| 2006/0135967 A1 | 6/2006 | Realyvasquez |
| 2006/0136044 A1 | 6/2006 | Osborne |
| 2006/0136045 A1 | 6/2006 | Flagle |
| 2006/0136052 A1 | 6/2006 | Vesely |
| 2006/0136054 A1 | 6/2006 | Berg |
| 2006/0142846 A1 | 6/2006 | Pavcnik |
| 2006/0142847 A1 | 6/2006 | Shaknovich |
| 2006/0142848 A1 | 6/2006 | Gabbay |
| 2006/0142854 A1 | 6/2006 | Alferness |
| 2006/0149358 A1 | 7/2006 | Zilla |
| 2006/0149360 A1 | 7/2006 | Schwammenthal |
| 2006/0149367 A1 | 7/2006 | Sieracki |
| 2006/0149368 A1 | 7/2006 | Spence |
| 2006/0161133 A1 | 7/2006 | Laird |
| 2006/0161248 A1 | 7/2006 | Case |
| 2006/0161249 A1 | 7/2006 | Realyvasquez |
| 2006/0161250 A1 | 7/2006 | Shaw |
| 2006/0167468 A1 | 7/2006 | Gabbay |
| 2006/0167541 A1 | 7/2006 | Lattouf |
| 2006/0167542 A1 | 7/2006 | Quintessenza |
| 2006/0167543 A1 | 7/2006 | Bailey |
| 2011/0251678 A1 | 10/2011 | Eidenschink |

FOREIGN PATENT DOCUMENTS

| | | |
|---|---|---|
| EP | 0604022 | 6/1994 |
| FR | 2728457 | 6/1996 |
| WO | 8800459 | 1/1988 |
| WO | 9015582 | 12/1990 |
| WO | 9501669 | 1/1995 |
| WO | 9619159 | 6/1996 |
| WO | 9803656 | 1/1998 |
| WO | 9846115 | 10/1998 |
| WO | 9904724 | 2/1999 |
| WO | 0067679 | 11/2000 |
| WO | 0115650 | 3/2001 |
| WO | 0117462 | 3/2001 |
| WO | 0166043 | 9/2001 |
| WO | 03047468 | 6/2003 |
| WO | 03084443 | 10/2003 |
| WO | 2004019825 | 3/2004 |
| WO | 2004021893 | 3/2004 |
| WO | 2004023980 | 3/2004 |
| WO | 2004030568 | 4/2004 |
| WO | 2004030569 | 4/2004 |
| WO | 2004030570 | 4/2004 |
| WO | 2004032724 | 4/2004 |

| | | | | | |
|---|---|---|---|---|---|
| WO | 2004032796 | 4/2004 | WO | 2005027797 | 3/2005 |
| WO | 2004037128 | 5/2004 | WO | 2005034812 | 4/2005 |
| WO | 2004037317 | 5/2004 | WO | 2005039428 | 5/2005 |
| WO | 2004039432 | 5/2004 | WO | 2005039452 | 5/2005 |
| WO | 2004043265 | 5/2004 | WO | 2005046488 | 5/2005 |
| WO | 2004043273 | 5/2004 | WO | 2005046528 | 5/2005 |
| WO | 2004043293 | 5/2004 | WO | 2005046529 | 5/2005 |
| WO | 2004045370 | 6/2004 | WO | 2005046530 | 5/2005 |
| WO | 2004045378 | 6/2004 | WO | 2005046531 | 5/2005 |
| WO | 2004045463 | 6/2004 | WO | 2005049103 | 6/2005 |
| WO | 2004047677 | 6/2004 | WO | 2005051226 | 6/2005 |
| WO | 2004060217 | 7/2004 | WO | 2005055811 | 6/2005 |
| WO | 2004060470 | 7/2004 | WO | 2005055883 | 6/2005 |
| WO | 2004062725 | 7/2004 | WO | 2005058206 | 6/2005 |
| WO | 2004066803 | 8/2004 | WO | 2005065585 | 7/2005 |
| WO | 2004066826 | 8/2004 | WO | 2005065593 | 7/2005 |
| WO | 2004069287 | 8/2004 | WO | 2005065594 | 7/2005 |
| WO | 2004075789 | 9/2004 | WO | 2005070342 | 8/2005 |
| WO | 2004080352 | 9/2004 | WO | 2005070343 | 8/2005 |
| WO | 2004082523 | 9/2004 | WO | 2005072654 | 8/2005 |
| WO | 2004082527 | 9/2004 | WO | 2005072655 | 8/2005 |
| WO | 2004082528 | 9/2004 | WO | 2005079706 | 9/2005 |
| WO | 2004082536 | 9/2004 | WO | 2005082288 | 9/2005 |
| WO | 2004082537 | 9/2004 | WO | 2005082289 | 9/2005 |
| WO | 2004082538 | 9/2004 | WO | 2005084595 | 9/2005 |
| WO | 2004082757 | 9/2004 | WO | 2005087139 | 9/2005 |
| WO | 2004084746 | 10/2004 | WO | 2005087140 | 9/2005 |
| WO | 2004084770 | 10/2004 | WO | 2006000763 | 1/2006 |
| WO | 2004089246 | 10/2004 | WO | 2006000776 | 1/2006 |
| WO | 2004089250 | 10/2004 | WO | 2006002492 | 1/2006 |
| WO | 2004089253 | 10/2004 | WO | 2006004679 | 1/2006 |
| WO | 2004091449 | 10/2004 | WO | 2006005015 | 1/2006 |
| WO | 2004091454 | 10/2004 | WO | 2006009690 | 1/2006 |
| WO | 2004093638 | 11/2004 | WO | 2006011127 | 2/2006 |
| WO | 2004093726 | 11/2004 | WO | 2006012011 | 2/2006 |
| WO | 2004093728 | 11/2004 | WO | 2006012013 | 2/2006 |
| WO | 2004093730 | 11/2004 | WO | 2006012038 | 2/2006 |
| WO | 2004093745 | 11/2004 | WO | 2006012068 | 2/2006 |
| WO | 2004093935 | 11/2004 | WO | 2006012322 | 2/2006 |
| WO | 2004096100 | 11/2004 | WO | 2006019498 | 2/2006 |
| WO | 2004103222 | 12/2004 | WO | 2006026371 | 3/2006 |
| WO | 2004103223 | 12/2004 | WO | 2006026377 | 3/2006 |
| WO | 2004105584 | 12/2004 | WO | 2006026912 | 3/2006 |
| WO | 2004105651 | 12/2004 | WO | 2006027499 | 3/2006 |
| WO | 2004112582 | 12/2004 | WO | 2006028821 | 3/2006 |
| WO | 2004112585 | 12/2004 | WO | 2006029062 | 3/2006 |
| WO | 2004112643 | 12/2004 | WO | 2006031436 | 3/2006 |
| WO | 2004112652 | 12/2004 | WO | 2006031469 | 3/2006 |
| WO | 2004112657 | 12/2004 | WO | 2006032051 | 3/2006 |
| WO | 2004112658 | 12/2004 | WO | 2006034245 | 3/2006 |
| WO | 2005000152 | 1/2005 | WO | 2006035415 | 4/2006 |
| WO | 2005002424 | 1/2005 | WO | 2006041505 | 4/2006 |
| WO | 2005002466 | 1/2005 | WO | 2006044679 | 4/2006 |
| WO | 2005004753 | 1/2005 | WO | 2006048664 | 5/2006 |
| WO | 2005007017 | 1/2005 | WO | 2006050459 | 5/2006 |
| WO | 2005007018 | 1/2005 | WO | 2006050460 | 5/2006 |
| WO | 2005007036 | 1/2005 | WO | 2006054107 | 5/2006 |
| WO | 2005007037 | 1/2005 | WO | 2006054930 | 5/2006 |
| WO | 2005048883 | 1/2005 | WO | 2006055982 | 5/2006 |
| WO | 2005009285 | 2/2005 | WO | 2006060546 | 6/2006 |
| WO | 2005009286 | 2/2005 | WO | 2006063108 | 6/2006 |
| WO | 2005009505 | 2/2005 | WO | 2006063181 | 6/2006 |
| WO | 2005009506 | 2/2005 | WO | 2006063199 | 6/2006 |
| WO | 2005011473 | 2/2005 | WO | 2006064490 | 6/2006 |
| WO | 2005011534 | 2/2005 | WO | 2006065212 | 6/2006 |
| WO | 2005011535 | 2/2005 | WO | 2006065930 | 6/2006 |
| WO | 2005013860 | 2/2005 | WO | 2006066148 | 6/2006 |
| WO | 2005018507 | 3/2005 | WO | 2006066150 | 6/2006 |
| WO | 2005021063 | 3/2005 | WO | 2006069094 | 6/2006 |
| WO | 2005023155 | 3/2005 | WO | 2006070372 | 7/2006 |
| WO | 2005025644 | 3/2005 | WO | 2006073628 | 7/2006 |
| WO | 2005027790 | 3/2005 | WO | 2006076890 | 7/2006 |

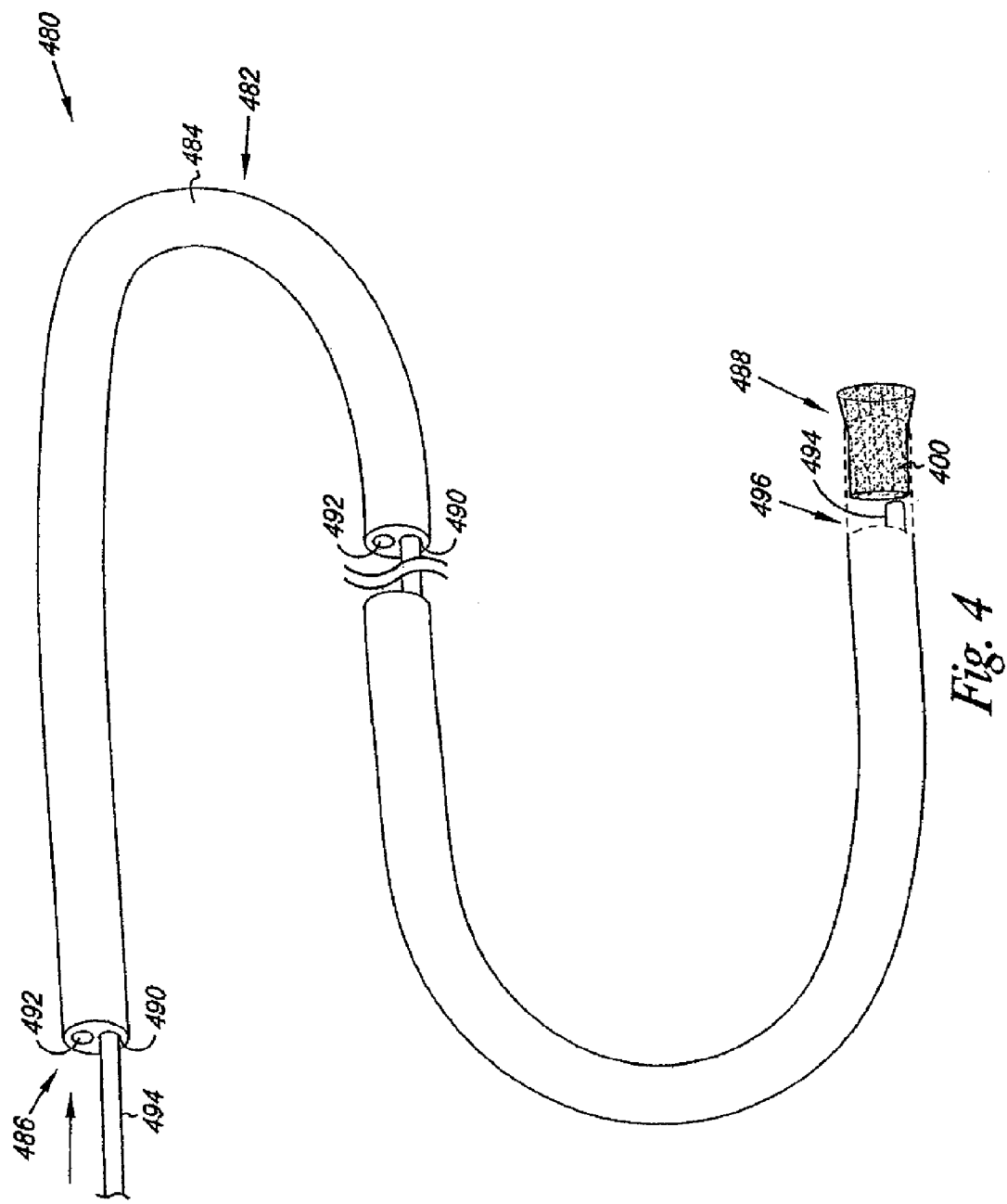

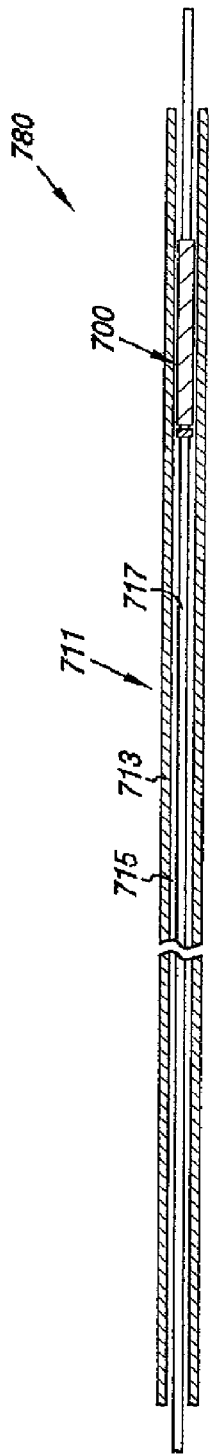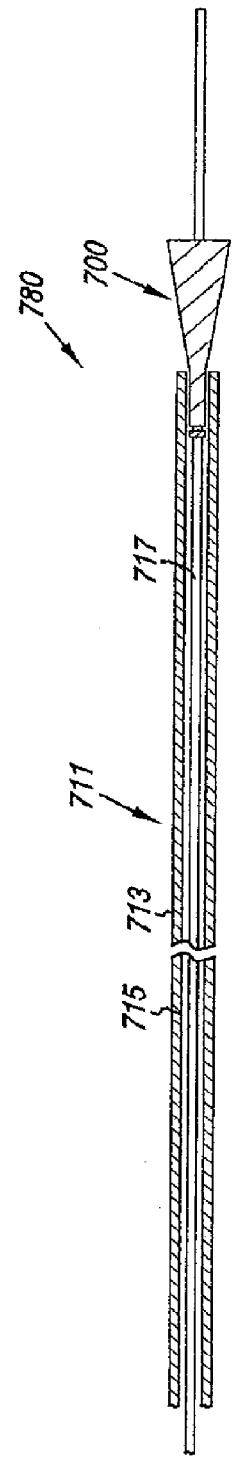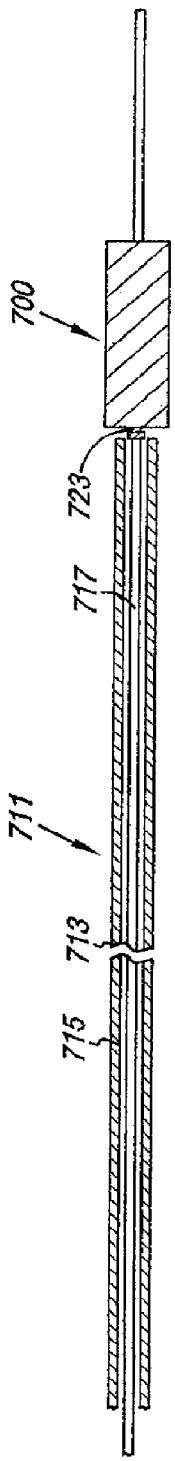
Fig. 7A
Fig. 7B
Fig. 7C

VENOUS VALVE, SYSTEM, AND METHOD WITH SINUS POCKET

CROSS REFERENCE TO RELATED APPLICATIONS

This application is a continuation of U.S. application Ser. No. 12/509,604, filed on Jul. 27, 2009, which is a continuation of U.S. application Ser. No. 11/232,403, filed on Sep. 21, 2005, now U.S. Pat. No. 7,569,071, the entire contents of each hereby incorporated by reference.

FIELD OF THE DISCLOSURE

The present disclosure relates to vascular medical devices, systems and methods; and more particularly to venous valves including a venous valve frame, and methods for forming and using the venous valve frame.

BACKGROUND OF THE DISCLOSURE

The venous system of the legs uses valves and muscles as part of the body's pumping mechanism to return blood to the heart. Venous valves create one way flow to prevent blood from flowing away from the heart. When valves fail, blood can pool in the lower legs resulting in swelling and ulcers of the leg. The absence of functioning venous valves can lead to chronic venous insufficiency.

Techniques for both repairing and replacing the valves exist, but are tedious and require invasive surgical procedures. Direct and indirect valvuoplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site.

Prosthetic valves can be transplanted into the venous system, but current devices are not successful enough to see widespread usage. One reason for this is the very high percentage of prosthetic valves reported with leaflet functional failures. These failures have been blamed primarily on improper sizing and tilted deployment of the prosthetic valve. In addition, a great number of leaflets of the prosthetic valves ultimately become fused to the vein wall.

BRIEF DESCRIPTION OF THE DRAWINGS

FIG. 4 illustrates an embodiment of a system that includes a valve according to the present disclosure.

FIGS. 7A, 7B and 7C illustrate an embodiment of a system that includes a valve according to the present disclosure.

DETAILED DESCRIPTION

Figure 1A:
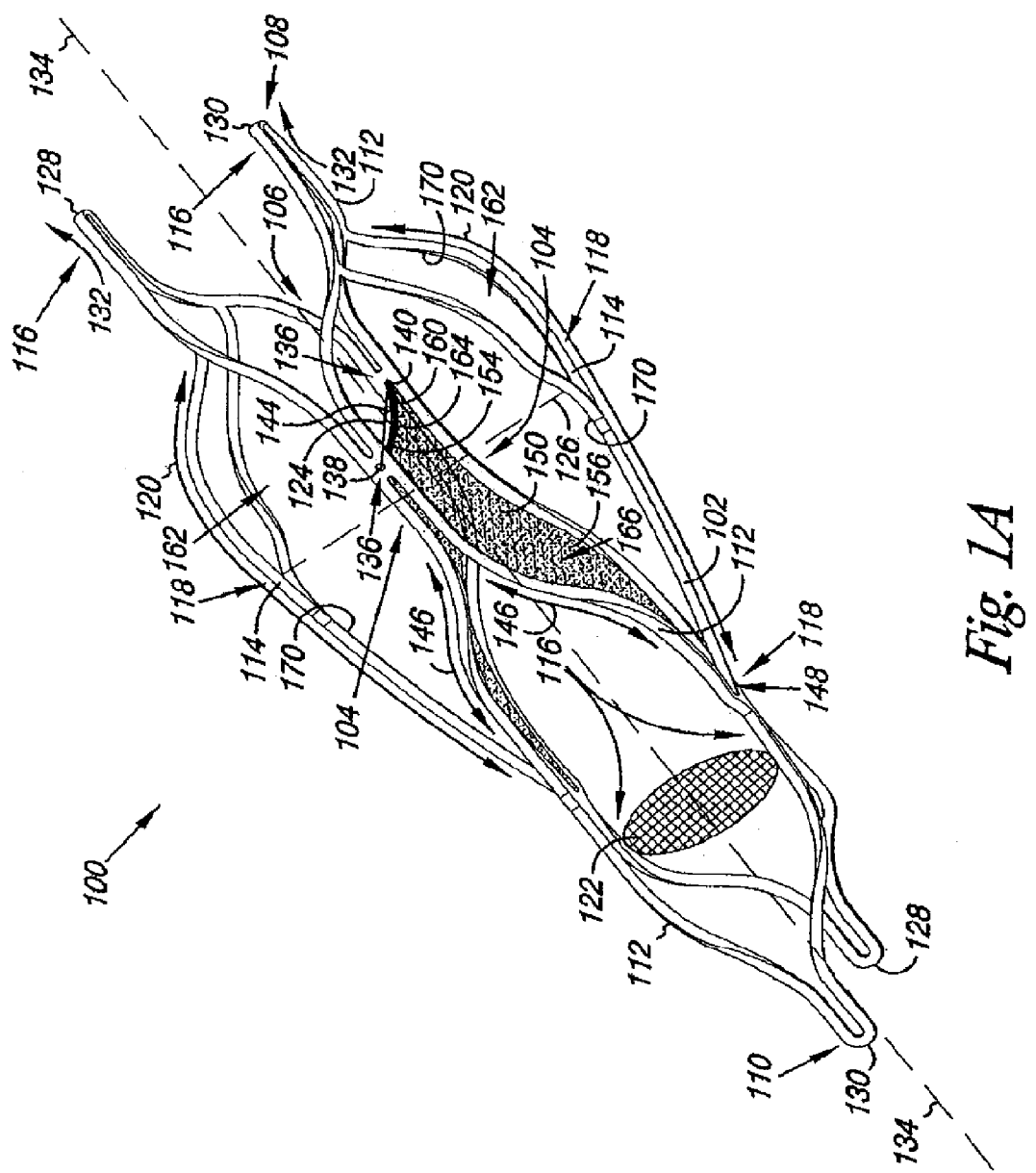
FIGS. 1A and 1B illustrate an embodiment of a venous valve according to the present disclosure.

Embodiments of the present disclosure are directed to vascular medical devices, systems and methods for valve replacement and/or augmentation. Particularly, the present disclosure provides venous valve frames, venous valves that utilize the venous valve frames, and methods for forming and using the venous valve frame and the venous valve. Various embodiments of the present disclosure can be used to replace and/or augment an incompetent valve in a body lumen.

Embodiments of the venous valve include a venous valve frame and valve leaflets that can be implanted through minimally-invasive techniques into the body lumen. In one example, embodiments of the apparatus, system, and method for valve replacement or augmentation may help to maintain antegrade blood flow, while decreasing retrograde blood flow in a venous system of individuals having venous insufficiency, such as venous insufficiency in the legs. Use of valve embodiments can also be possible in other portions of the vasculature.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of valve. In addition, discussion of features and/or attributes for an element with respect to one Fig. can also apply to the element shown in one or more additional Figs. Embodiments illustrated in the figures are not necessarily to scale.

Figure 1B:
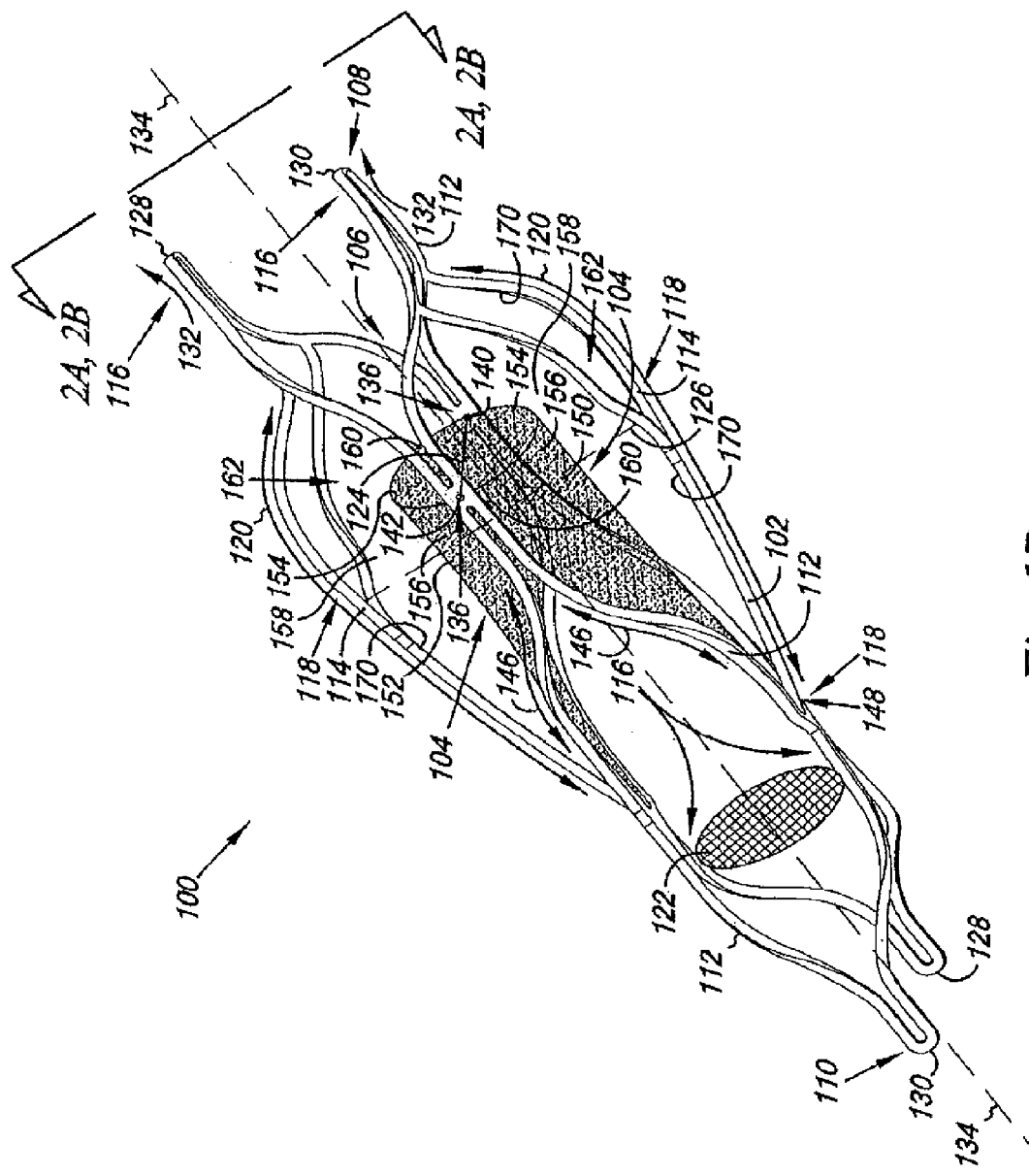

FIGS. 1A and 1B provide illustrations of various embodiments of a venous valve 100 of the present disclosure. The venous valve 100 can be implanted within the fluid passageway of a body lumen, such as for replacement and/or augmentation of a valve structure within the body lumen (e.g., a venous valve). In one embodiment, the venous valve 100 of the present disclosure may be beneficial to regulate the flow of a bodily fluid through the body lumen in a single direction.

FIGS. 1A and 1B illustrate one embodiment of the venous valve 100. Venous valve 100 includes a venous valve frame 102 and valve leaflets 104. In one embodiment, the valve frame 102 and the valve leaflets 104 of the venous valve 100 can resiliently radially collapse and expand, as will be described herein. Among other things, the valve frame 102 and the valve leaflets 104 define a lumen 106 of the venous valve 100. The lumen 106 allows for, amongst other things, fluid (e.g., blood) to move through the venous valve 100.

The valve frame 102 includes a first end 108 and a second end 110 opposite the first end 108. The first end 108 and the second end 110 define a length of the valve frame 102 and of the venous valve 100. In one embodiment, the length of venous valve 100 can have a number of values. As will be appreciated, the length of venous valve 100 can be determined based upon the location into which the venous valve 100 is to be implanted. In other words, the length of the venous valve 100 can be patient specific. Examples of values for the length include, but are not limited to, 20 millimeters to 80 millimeters. Other values are also possible.

The valve frame 102 can be formed in a wide variety of configurations. For example, the valve frame 102 can include a first structural member 112 and a second structural member 114 that together form a unitary structure with an open frame configuration. In one embodiment, the first structural member 112 defines an elongate base portion 116 that extends between the first end 108 and the second end 110 of the valve frame 102. As illustrated, the first structural member 112 defines openings through the valve frame 102 to provide at least a portion of the open frame configuration.

In addition, the first structural member 112 also defines a first perimeter value for the elongate base portion 116. In one embodiment, the first perimeter value can be essentially constant for the length of the valve frame 102. In other words, the outer limit of the area defined by the elongate base portion 116 remains essentially constant along the length of the valve frame 102. For example, an outer surface 118 of the first structural member 112 can define a circular cross-sectional area for the elongate base portion 116. As will be appreciated, other cross-sectional shapes are also possible, including but not limited to oval or elliptical.

In an alternative embodiment, the perimeter value changes along the length of the valve frame 102. For example, the outer surface 118 of the first structural member 112 can change from a first cross-sectional area having a first value for the elongate base portion 116 adjacent the first end 108 and the second end 110 to a second cross-sectional area having a second value larger than the first value. In one embodiment, the second cross-sectional area of the outer surface 118 of the first structural member 112 can, in conjunction with the second structural member 114 provide for a circular or round cross-sectional shape. Other cross-sectional shapes are also possible.

In an additional embodiment, the second structural member 114 helps to define a bulbous portion 120 of the valve frame 102. As illustrated, the second structural member 114 extends radially and longitudinally from the outer surface 118 of an area 122 defined by the first structural member 112 to form the bulbous portion 120. In one embodiment, the second structural member 114 helps to define a second perimeter value for the bulbous portion 120, where second perimeter value can be is greater than the first perimeter value.

As illustrated, the outer surface 118 of the first and second structural members 112, 114 can provide a perimeter of the bulbous portion 120 and the elongate base portion 116 having a predefined shape. For example, the first structural member 112 can define a first axis 124 of an elliptical shape and the second structural member 114 can define a second axis 126 of the elliptical shape. In one embodiment, the length of the second axis 126 can be at least twenty percent (20%) greater than the length of the first axis 124. In an additional embodiment, the length of the second axis 126 can be twenty percent (20%) to fifty percent (50%) greater than the length of the first axis 124. In a further embodiment, the length of the second axis 126 can be forty percent (40%) to forty-two percent (42%) greater than the length of the first axis 124.

In an additional embodiment, the length of the second axis 126 can be one (1) to four (4) millimeters greater than the length of the first axis 124. As will be more fully discussed herein, this allows for a gap of one-half (0.5) to two (2) millimeters to be maintained between a free edge of the valve leaflets 104 in their open configuration and the valve frame 102. In one embodiment, the length of the gap between each leaflet 104 and the valve frame 102 can be, but is not necessarily, equal.

In an additional example, the perimeter of the bulbous portion 120 and the elongate base portion 116 can have a round shape. For example, the first axis 124 of the first structure member 112 and the second axis 126 of the second structural member 114 can be essentially of equal length along the bulbous portion 120.

Figure 2A:
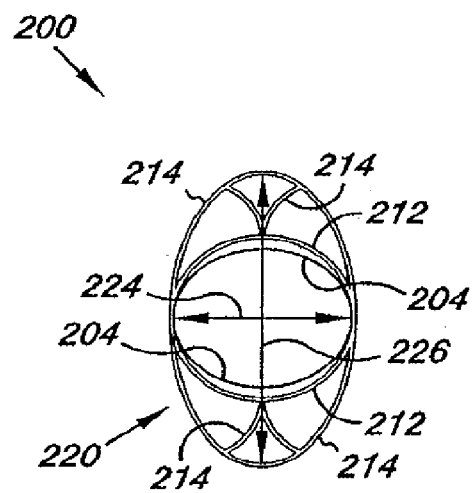
FIGS. 2A and 2B illustrate an end view of embodiments of a venous valve according to the present disclosure.
Figure 2B:
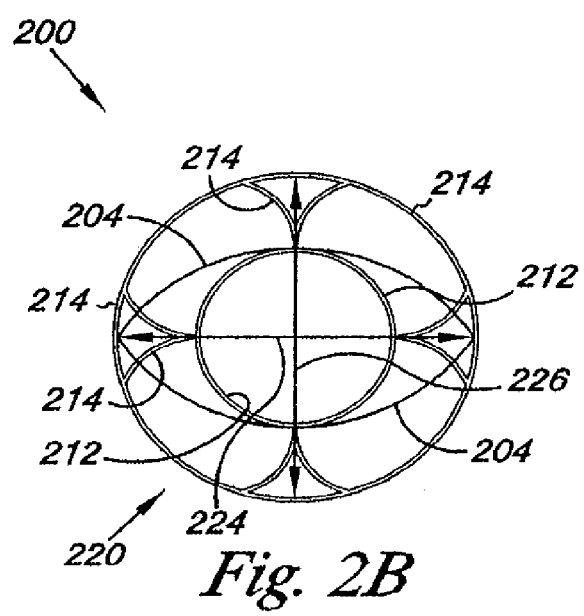
Figure 3A:
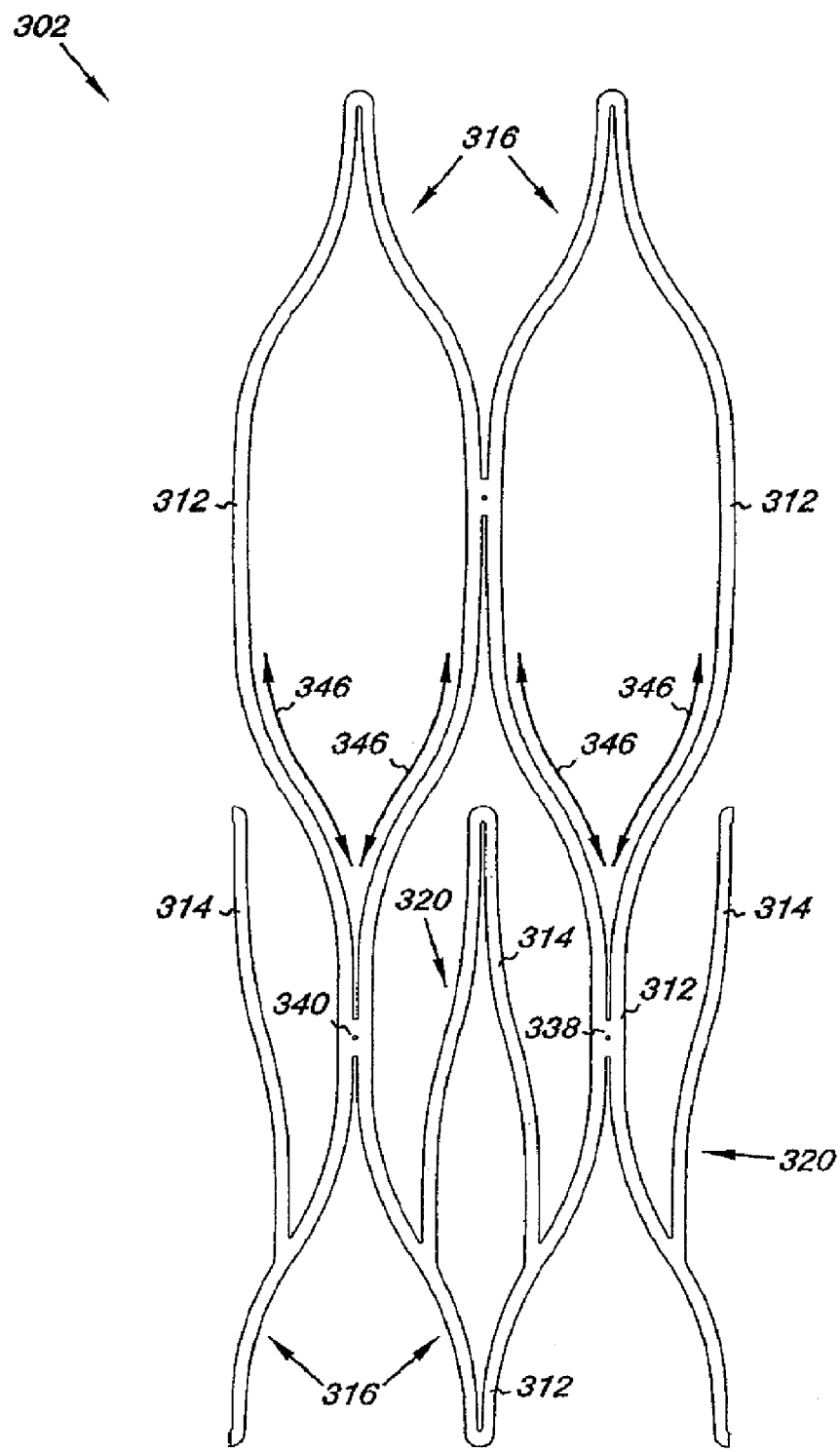
FIGS. 3A-3E illustrate embodiments of valve frame configurations according to the present disclosure.
Figure 3B:
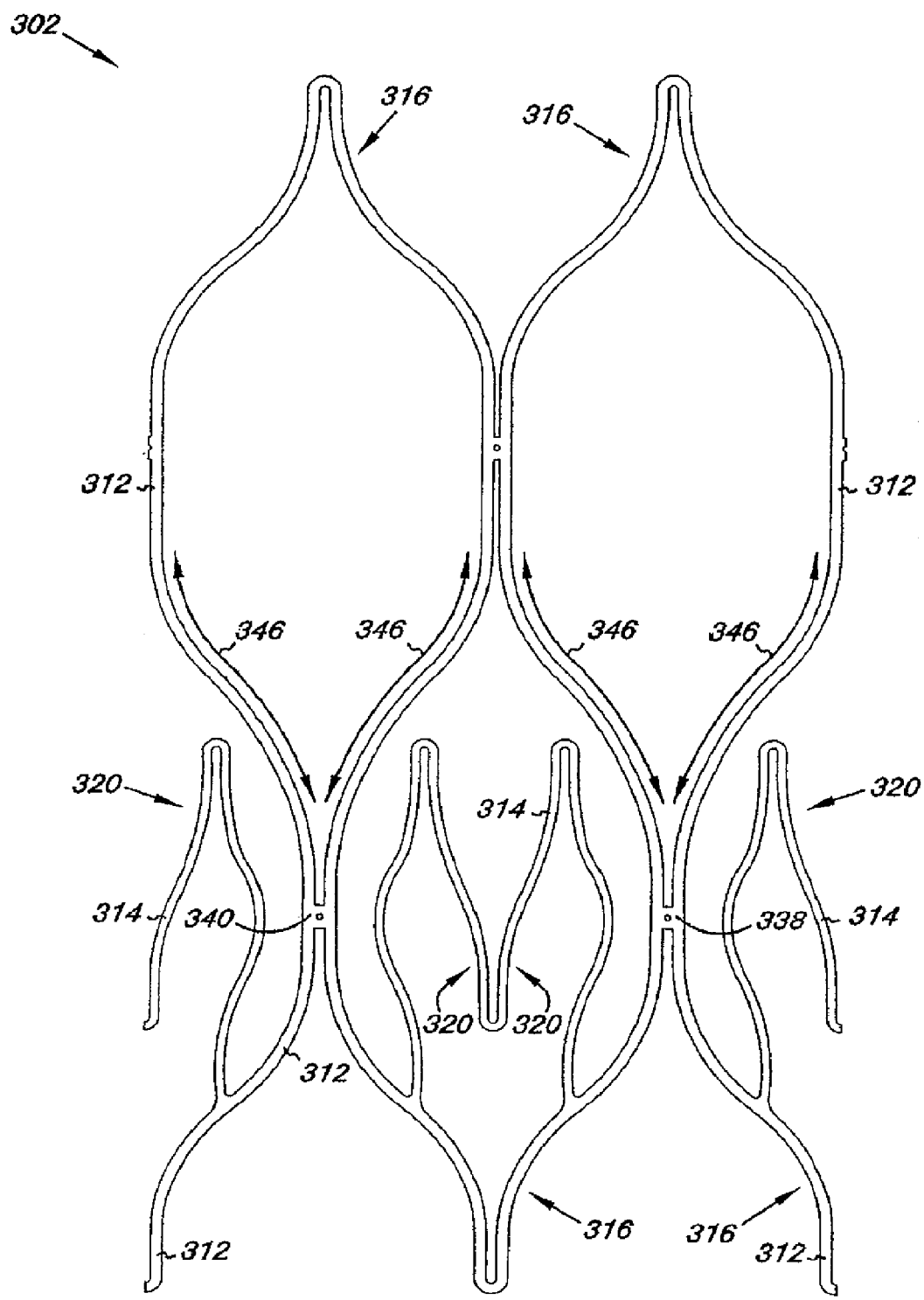
Figure 3C:
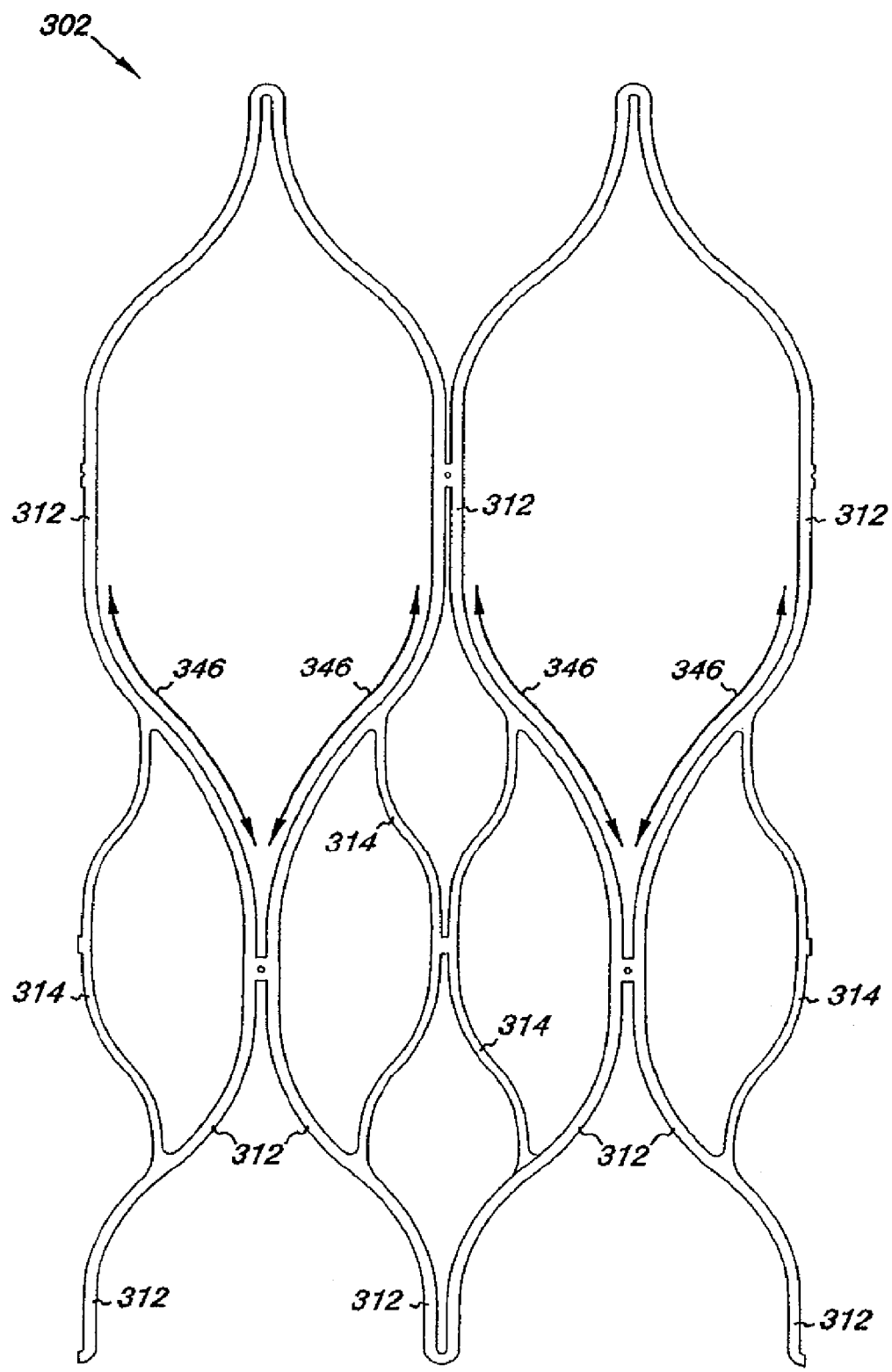
Figure 3D:
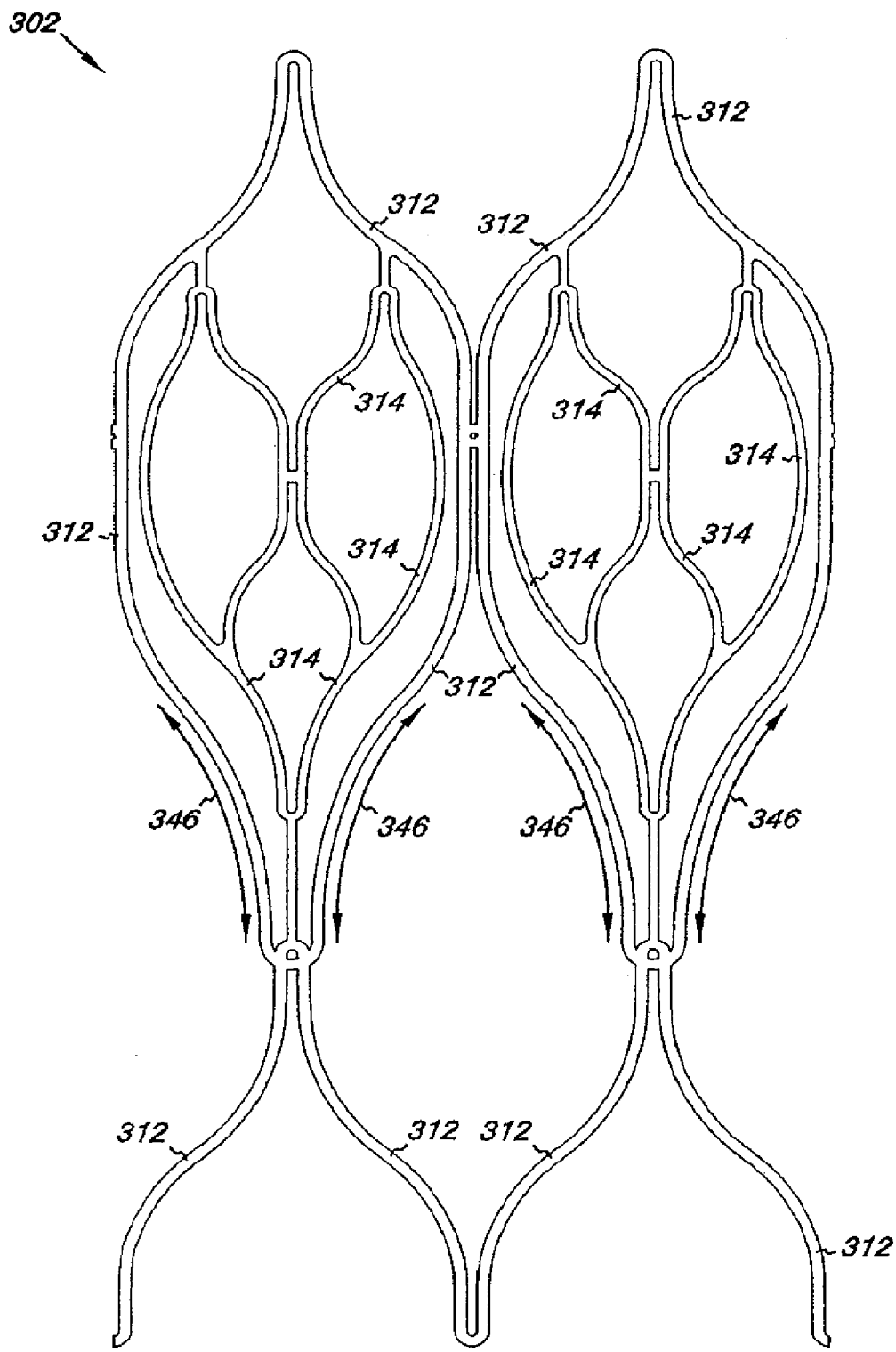
Figure 3E:
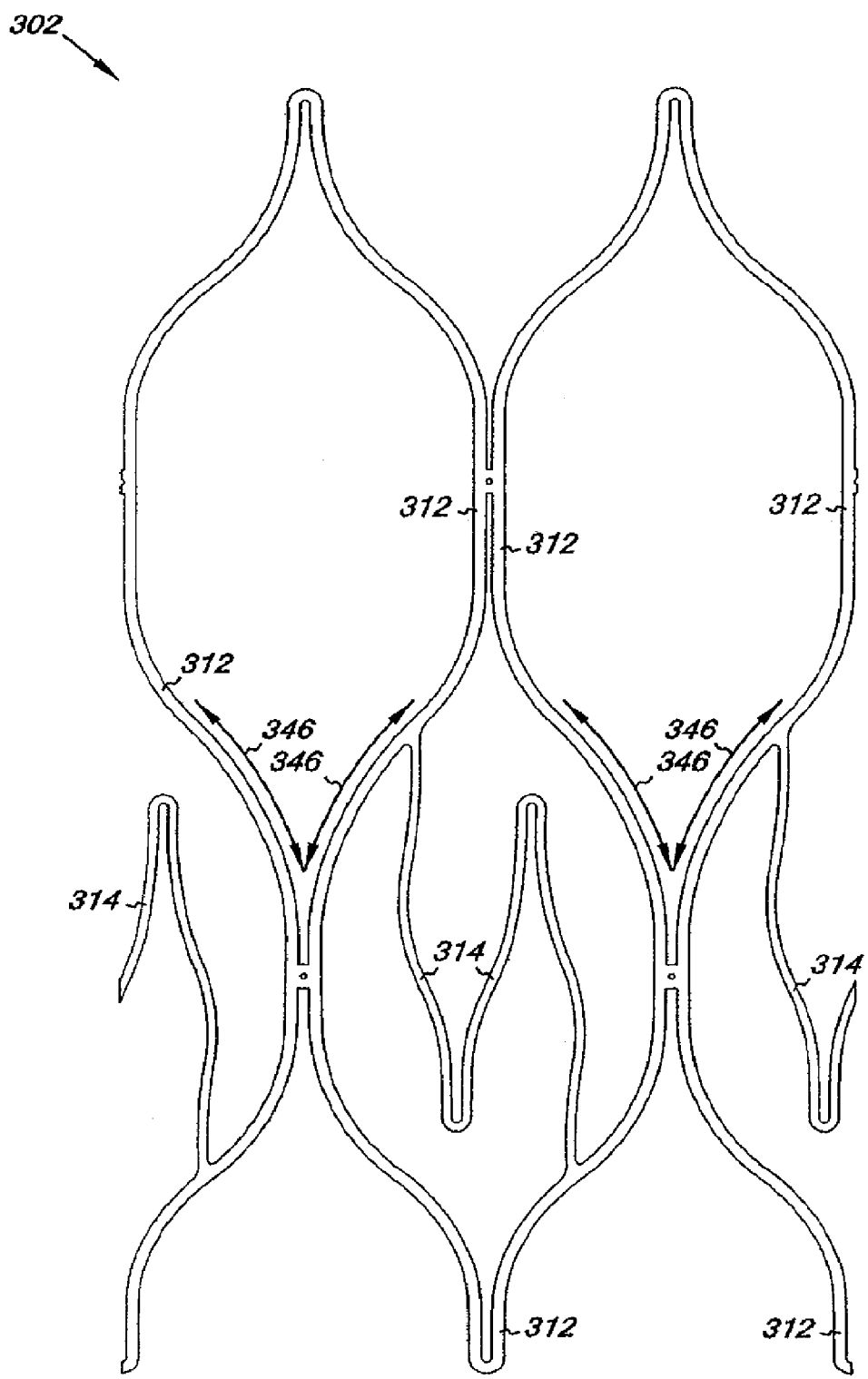

FIGS. 2A and 2B illustrate embodiments of the venous valve 200 according to the present disclosure. The embodiments illustrated in FIGS. 2A and 2B are end views of the venous valve illustrated in FIG. 1A taken along lines 2A-2A/ 2B-2B. As discussed herein, FIG. 2A illustrates the venous valve 200 where the first structural member 212 defining the first axis 224 and the second structural member 214 defining the second axis 226 provide an elliptical shape for the bulbous portion 220 of the valve frame 202. FIG. 2B illustrates the venous valve 200 where the first structural member 212 defining the first axis 224 and the second structural member 214 defining the second axis 226 provide a round shape for the bulbous portion 220 of the valve frame 202.

In addition, the first structural member 112 at each of the first end 108 and the second end 110 can include a first curve 128 and a second curve 130 opposite the first curve 128. In one embodiment, the first structural member 112 forming the first and second curve 128, 130 can move radially as the valve 100 radially collapses and expands. In the various embodiments described herein, the first and second curve 128, 130 can provide a spring force (e.g., elastic potential energy) to counter radial compression of the frame valve 102 towards its uncompressed state. As will be appreciated, the first and second curve 128, 130 can have a number of configurations, including turns defining angles and/or arcs (e.g., having a radius of curvature). Additional spring force can be imparted to the frame 102 from the compression of other portions of the valve frame 102 as well.

In one embodiment, the first and second curve 128, 130 at each of the ends 108, 110 can lay opposite each other on a respective plane that is parallel to the other plane. In addition, the first and second curve 128, 130 of the first end 108 can be positioned radially orthogonal to the first and second curve 128, 130 of the second end 110 of the base portion 116. As will be appreciated, the first and second curve 128, 130 at each of the ends 108, 110, however, need not either lay on planes that are parallel relative each other and/or be positioned radially orthogonal to each other.

The compressible nature of the valve 100 can accommodate changes in body lumen size (e.g., diameter of the body lumen) by flexing to expand and/or contract to change the diameter of the valve frame 102. In one embodiment, the first and second curve 128, 130 in the first structural member 112 can act as springs to allow the valve 100 to resiliently radially collapse and expand. The frame 102 can also provide sufficient contact and expansion force with the surface of a body lumen wall to encourage fixation of the valve 100 and to prevent retrograde flow within the body lumen around the edges of the frame 102 and the surface of a lumen when combined with a closed state of the valve leaflets attached thereto. Anchoring elements (e.g., barbs) can also be included with valve 100.

As will be appreciated, the first and second curve 128, 130 in the first structural member 112 can also include, but are not limited to, other shapes that allow for repeatable travel between the collapsed state and the expanded state. For example, the elastic regions can include integrated springs having a circular or an elliptical loop configuration. The embodiments are not, however, limited to these configurations as other shapes are also possible.

The first structural member 112 forming the first and second curve 128, 130 can also include a radial flare 132 that curves away from a center longitudinal axis 134. As illustrated, the radial flare 132 provides for an increase in the peripheral frame dimension at the first end 108 and/or the second end 110 of the valve frame 102. In one embodiment, the first structural member 112 can be pre- and/or post-treated to impart the radial flare 132. For example, the first structural member 112 forming the first and second curve 128, 130 of the valve frame 102 could be bent to impart the radial flare 132. The frame 102 could then be heat treated so as to fix the radial flare 132 into the first structural member 112. Other material treatments (e.g., plastic deformation, forging, elastic deformation with heat setting) are also possible to impart the radial flare as described herein, many of which are material specific.

The first structural member 112 and/or the second structural member 114 of the valve frame 102 can have similar and/or different cross-sectional geometries and/or cross-sectional dimensions along their length. The similarity and/or the differences in the cross-sectional geometries and/or cross-sectional dimensions can be based on one or more desired functions to be elicited from each portion of the frame 102. For example, the first structural member 112 and/or the second structural member 114 can have a similar cross-sectional geometry along its length. Examples of cross-sectional geometries include, but are not limited to, round (e.g., circular, oval, and/or elliptical), rectangular geometries having perpendicular sides, one or more convex sides, or one or more concave sides; semi-circular; triangular; tubular; I-shaped; T-shaped; and trapezoidal.

Alternatively, the cross-sectional dimensions of one or more geometries of the first structural member 112 and/or the second structural member 114 can change from one portion of the frame 102 to another portion of the frame 102. For example, portions of the first structural member 112 and/or the second structural member 114 can taper (i.e., transition) from a first geometric dimension to a second geometric dimension different than the first geometric dimension. These embodiments, however, are not limited to the present examples as other cross-sectional geometries and dimension are also possible. As such, the present disclosure should not be limited to the frames provided in the illustration herein.

The valve frame 102 further includes a valve leaflet connection location 136 along the first structural member 112 of the valve frame 102. In one embodiment, the valve leaflet connection location 136 includes portions of the first structural member 112 that can define the area 122, as well as surfaces of the first structural member 112 that define openings through the frame 102. For example, the first structural member 112 can include surfaces that define a first opening 138 and a second opening 140 for the valve leaflet connection location 136. In one embodiment, the first and second openings 138, 140 are adjacent a region of the bulbous portion 120 of the valve frame 102. The first and second openings 138, 140 are also illustrated as being positioned opposite each other along a common axis 144. In the present illustration, the common axis 144 is along the first axis 124 of the shape (e.g., elliptical, round) formed by the first and second structural member 112, 114.

In an additional embodiment, the valve leaflet connection location 136 further includes a predefined portion 146 along the first structural member 112 to which the valve leaflets 104 can be attached. As illustrated, the predefined portion 146 includes a portion of the first structural member 112 that extends between the first and second openings 138, 140 in the region of the bulbous portion 120. In one embodiment, the valve leaflets 104 can be coupled to the valve frame 102 through the first and second openings 138, 140 and the predefined portion 146 of the first structural member 112.

In addition to allowing the valve leaflets 104 to be coupled to the valve frame 102, the valve leaflet connection location 140 can also include predetermined dimensional relationships between portions of the valve leaflet connection location 136. For example, predetermined dimensional relationships can exist between the relative positions of the first and second openings 138, 140 and the predefined portion 146 of the first structural member 112. These dimensional relationships can help to better position the valve leaflets 104 in relation to the bulbous portion 120 of the valve frame 102.

For example, as illustrated the predefined portion 146 of the first structural member 112 extends away from the first and second opening 138, 140 to define a distal point 148 from the first and second openings 138, 140. In one embodiment, the distance between the first and second openings 138, 140 and a plane that is both orthogonal to the center longitudinal axis 134 and in contact with the distal point 148 is a predetermined length having a value of eighty-five percent (85%) of distance of the second axis 126.

In one embodiment, the valve leaflets 104 include a first valve leaflet 150 and a second valve leaflet 152. As illustrated, the first and second valve leaflets 150, 152 are connected to the valve leaflet connection location 136. The first and second valve leaflet 150, 152 have surfaces that define a commissure 154 that reversibly opens and closes for unidirectional flow of a liquid through the venous valve 100. As used herein, the commissure 154 includes portions of the valve leaflet 104 surfaces that reversibly form a connection to allow fluid to flow through the valve 100 in essentially one direction. For example, the surfaces of the first and second valve leaflets 150, 152 can move between a closed configuration in which fluid flow through the lumen 106 can be restricted and an open configuration in which fluid flow through the lumen 106 can be permitted.

In addition, the first and second openings 138, 140 can be radially symmetric around the longitudinal central axis 134 of the valve frame 102. As illustrated, the first and second openings 138, 140 can be positioned approximately one hundred eighty (180) degrees relative each other around the longitudinal central axis 134 of the frame 102. As will be appreciated, the first and second openings 138, 140 need not necessarily display an equally spaced symmetrical relationship as described above in order to practice the embodiments of the present disclosure. For example, the radial relationship can have the first and second openings 138, 140 positioned at values greater than one hundred eighty (180) degrees and less than one hundred eighty (180) degrees relative each other around the longitudinal central axis 134 of the frame 102.

In the present example, the first and second valve leaflet 150, 152 can be coupled, as described more fully herein, to at least the valve leaflet connection location 136 and the predefined portion 146 of the valve frame 102. As illustrated, the valve leaflets 104 include a region 156 of the valve leaflets 104 that can move relative the valve frame 102. The region 156 of the valve leaflets 104 can be unbound (i.e., unsupported) by the frame 102 and extends between the first and second openings 138, 140. This configuration permits the first and second valve leaflet 150, 152 to move (e.g., pivot) relative the first and second openings 138, 140 to allow the commissure 154 to reversibly open and close for unidirectional flow of the liquid through the venous valve 100.

In an additional embodiment, the valve leaflets 104 in their open configuration have a circumference that is less than the circumference of the valve frame 102. For example, as illustrated, the valve leaflets 104 in their open configuration include a gap 158 between a free edge 160 of the first and second valve leaflets 150, 152 and the bulbous portion 120 of the valve frame 102. As discussed herein, the length of the second axis 126 can be one (1) to four (4) millimeters greater than the length of the first axis 124. In one embodiment, this allows for the gap 158 between the free edge 160 of each valve leaflet 104 in their open position to be one-half (0.5) to two (2) millimeters from the bulbous portion 120 of the valve frame 102. In one embodiment, the length of the gap 158 between each leaflet 104 and the valve frame 102 can be, but is not necessarily, equal.

In one embodiment, the first and second valve leaflets 150, 152 and the bulbous portion 120 of the valve frame 102 provide surfaces that define a sinus pocket 162. As illustrated, the sinus pocket 162 provides a dilated channel or receptacle as compared to the elongate base portion 116 of the venous valve 100. In one embodiment, the presence of the sinus pocket 162 better ensures that the valve leaflets 104 do not come into contact with a significant portion of the valve frame 102 and/or the inner wall of the vessel in which the valve 100 is implanted. For example, the sinus pocket 162 can help prevent adhesion between the valve leaflets 104 and the vessel wall due to the presence of a volume of blood there between.

The sinus pocket 162 can also allows for improved valve leaflets 104 dynamics (e.g., opening and closing of the valve leaflets 104). For example, the sinus pocket 162 can allow for pressure differentials across the surfaces of the valve leaflets 104 that provide for more rapid closing of the valve leaflets 104 as the retrograde blood flow begins, as will be discussed herein.

In one embodiment, the free edge 160 of the first and second valve leaflets 150, 152 is adjacent the commissure 154. In one embodiment, the free edge 160 has a surface that defines a curve 164 between the first and second openings 138, 140. The curve 164 also has a bottom 166 relative the first and second openings 138, 140. The free edge 160 can have either a non-planar or a planar configuration. As illustrated, the free edge 160 of the first and second leaflets 150, 152 define the bottom 166 of the curve 164 that is at least a predetermined distance away from the second structural member 114 so as to define the gap 158 between the first and second leaflet 150, 152 and the second structural member 114.

In one embodiment, whether the free edge 160 has a planar or non-planar configuration can depend on what material is selected for forming the valve leaflets 104. For example, when a stiffer material (e.g., PTFE) is used for the valve leaflets 104 the free edge 160 can have more of a concave shape than a planar or straight shape. In other words, as illustrated in FIG. 1A, the free edge 160 transitions from a first position adjacent the first and second openings 138, 140 to a second position lower than the first position as illustrated approximately midway between the first and second openings 138, 140. So, the free edge 160 dips down to a low point approximately midway between and relative to the first and second openings 138, 140. In one embodiment, this shape allows the free edge 160 to form a catenary when the valve leaflets 104 are in their closed position, as illustrated in FIG. 1A. In an alternative embodiment, when an elastic material is used for the valve leaflets 104 the free edge 160 has more of a straight or planar shape. In other words, the free edge 160 maintains essentially the same relative position around the circumference of the valve leaflets 104.

In addition, the dimensions and configuration of the valve leaflets 104 can further include proportional relationships to structures of the valve frame 102. For example, the first and second leaflets 150, 152 can each have a predetermined length between the distal point 148 and the bottom 166 of the curve 164 that is at least fifty percent (50%) greater than a radius of the elongate base portion 116. In one embodiment, this dimensional relationship is taken when the valve leaflets 104 are in their closed position.

In addition to allowing the valve leaflets 104 to be coupled to the valve frame 102, the valve leaflet connection location 136 can also include predetermined dimensional relationships between portions of the valve leaflet connection location 136. For example, predetermined dimensional relationships can exist between the relative positions of the first and second openings 138, 140 and the predefined portion 146 of the first structural member 112. These dimensional relationships can help to better position the valve leaflets 104 in relation to the bulbous portion 120 of the valve frame 102.

In an additional embodiment, a predetermined portion of the surfaces of the valve leaflets 150, 152 that contact to define the commissure 154 can extend parallel to the center longitudinal axis 134 of the venous valve 100 when the valve 100 is in its closed configuration (FIG. 1A). For example, the predetermined portion of the surfaces of the valve leaflets 150, 152 can include twenty percent (20%) of the predetermined length of the valve leaflets 150, 152 between the distal point 148 and the bottom 166 of the curve 164. In other words, at least twenty percent (20%) of the length of the valve leaflet 150, 152 surfaces contact to form the commissure 154.

As will be appreciated, the free edge 160 when the valve leaflets 104 are in their open configuration can have a non-round shape. For example, the free edge 160 can have an eye shape or an oval shape with the second axis extending between the first and second openings 138, 140. As will be appreciated, other shapes for the valve leaflets 104 in their open configuration are also possible, including a round shape.

In one embodiment, under antegrade fluid flow (i.e., positive fluid pressure) from the second end 110 towards the first end 108 of the valve 100, the valve leaflets 104 can expand toward the inner surface 170 of the bulbous portion 120 of the frame 102 to create an opening through which fluid is permitted to move. In one example, the valve leaflets 104 each expand to define a semi-tubular structure having an oval cross-section when fluid opens the commissure 154.

As discussed herein, in the open configuration the gap 158 exists between the free edge 160 of the first and second valve leaflets 150, 152 and the bulbous portion 120 of the valve frame 102. In one embodiment, the size and shape of the valve leaflets 104 provides the gap 158 thereby preventing the valve leaflets 104 from touching the vein wall.

In addition, the size and shape of the valve leaflets 104 along with the gap 158 provides for more responsive opening and closing of the commissure 154 due to hydrodynamic relationships that are formed across the valve leaflets 104. For example, as the leaflets 104 are not in contact with the vessel wall and/or the bulbous portion 120 of the frame 102, the leaflets 104 can be more responsive to changes in the flow direction. The presence of the sinus pocket 162 allows slower moving fluid (e.g., blood) to move into the pocket and faster moving blood on the flow side of the leaflet 104 to create a pressure differential. This pressure differential across the valve leaflets 104 provides for the Bernoulli effect for which an increase in fluid flow velocity there occurs simultaneously a decrease in pressure. So, as fluid flow becomes retrograde the fluid velocity through the opening of the valve leaflets 104 is larger than the fluid flow in the sinus pocket 162. As a result, there is a lower pressure in the opening of the valve leaflets 104 that causes the opening to close more quickly as compared to valves without the sinus pocket 162.

In an additional embodiment, the configuration of the present embodiments allows the leaflets 104 to experience a low shear as compared to angled leaflets which are subject to high shear and direct impact with flowing blood. This can be attributed to the alignment of the valve leaflets 104 with the elongate base portion 116, and the adjacent vein segment, above and below the sinus pocket 162. The sinus pocket 162 also allows for recirculation of blood within the pocket 162 that cleans out potential thrombus buildup in the bottom of the pocket 162.

Valve 100 provides an embodiment in which the surfaces defining the commissure 154 provide a bi-leaflet configuration (i.e., a bicuspid valve) for valve 100. Although the embodiments in FIGS. 1A and 1B illustrate and describe a bi-leaflet configuration for the valve of the present disclosure, designs employing a different number of valve leaflets (e.g., tri-leaflet valve) may be possible. For example, additional connection points (e.g., three or more) could be used to provide additional valve leaflets (e.g., a tri-leaflet valve).

The embodiments of the frame described herein can also be constructed of one or more of a number of materials and in a variety of configurations. The frame embodiments can have a unitary structure with an open frame configuration. The frame can also be self-expanding. Examples of self-expanding frames include those formed from temperature-sensitive memory alloy which changes shape at a designated temperature or temperature range, such as Nitinol. Alternatively, the self-expanding frames can include those having a spring-bias. In addition, the valve frame 102 can have a configuration that allows the frame embodiments be radially expandable through the use of a balloon catheter. In this embodiment, the valve frame can be provided in separate pieces (e.g., two frame pieces) that are delivered individually to the implant site.

The embodiments of the frame 102 can also be formed from one or more contiguous frame members. For example, the first and second structural member 112, 114 of the frame 102 can be formed from a single contiguous member. The single contiguous member can be bent around an elongate tubular mandrel to form the frame. The free ends of the single contiguous member can then be welded, fused, crimped, or otherwise joined together to form the frame. In an additional embodiment, the first and second structural member 112, 114 of the frame 102 can be derived (e.g., laser cut, water cut) from a single tubular segment. In an alternative embodiment, methods of joining the first and second structural member 112, 114 of the frame 102 to create the elastic region include, but are not limited to, welding, gluing, and fusing the frame member. The frame 102 can be heat set by a method as is typically known for the material which forms the frame 102.

The valve frame 102 can be formed from a number of materials. For example, the frame can be formed from a biocompatible metal, metal alloy, polymeric material, or combination thereof. As described herein, the frame can be self-expanding or balloon expandable. In addition, the frame can be configured so as to have the ability to move radially between the collapsed state and the expanded state. Examples of suitable materials include, but are not limited to, medical grade stainless steel (e.g., 316L), titanium, tantalum, platinum alloys, niobium alloys, cobalt alloys, alginate, or combinations thereof. Additional frame embodiments may be formed from a shape-memory material, such as shape memory plastics, polymers, and thermoplastic materials. Shaped memory alloys having superelastic properties generally made from ratios of nickel and titanium, commonly known as Nitinol, are also possible materials. Other materials are also possible.

The lumen 106 can include a number of sizes. For example, the size of the lumen can be determined based upon the type of body lumen and the body lumen size in which the valve is to be placed. In an additional example, there can also be a minimum value for the width for the frame that ensures that the frame will have an appropriate expansion force against the inner wall of the body lumen in which the valve is being placed.

The valve 100 can further include one or more radiopaque markers (e.g., rivets, tabs, sleeves, welds). For example, one or more portions of the frame can be formed from a radiopaque material. Radiopaque markers can be attached to, electroplated, dipped and/or coated onto one or more locations along the frame. Examples of radiopaque material include, but are not limited to, gold, tantalum, and platinum.

The position of the one or more radiopaque markers can be selected so as to provide information on the position, location and orientation (e.g., axial, directional, and/or clocking position) of the valve during its implantation. For example, radiopaque markers can be configured radially and longitudinally (e.g., around and along portions of the first structural member 112) on predetermined portions of the valve frame 102 to allow the radial and axial position of the valve frame 102 to be determined. So in one embodiment a radiograph image of the valve frame 102 taken perpendicular to the valve leaflets 104 in a first clock position can produce a first predetermined radiograph image (e.g., an imaging having the appearance of an inverted "Y") and a radiographic image taken perpendicular to the first and second openings 138, 140 in a second clock position can produce a second predetermined radiograph image (e.g., an imaging having the appearance of an upright "Y") distinguishable from the first predetermined radiograph image.

In one embodiment, the first and second predetermined radiograph images allow the radial position of the leaflets 104 to be better identified within the vessel. This then allows a clocking position for the valve 100 to be determined so that the valve can be positioned in a more natural orientation relative the compressive forces the valve will experience in situ. In other words, determining the clocking of the valve as described herein allows the valve to be radially positioned in same orientation as native valve that it's replacing and/or augmenting.

In one embodiment, the material of the valve leaflets 104 can be sufficiently thin and pliable so as to permit radially-collapsing of the valve leaflets 104 for delivery by catheter to a location within a body lumen. The valve leaflets 104 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethylene (PE), polyethylene terephthalate (PET), silk, Rayon, Silicone, or the like. Possible biologic materials include, but are not limited to, autologous, allogeneic or xenograft material. These include explanted veins and decellularized basement membrane materials (such as non-crosslinked bladder membrane or amnionic membrane), such as small intestine submucosa (SIS) or umbilical vein. As will be appreciated, blends or mixtures of two or more of the materials provided herein are possible. For example, SIBS can be blended with one or more basement membrane materials.

As described herein, a number of methods exist for attaching the valve leaflets 104 to the valve frame 102. For example, when positioned over the inter surface 114 of the frame 102, the valve leaflets 104 can be secured to the frame members 118 through the use of biocompatible staples, glues, sutures or combinations thereof. In an additional embodiment, the valve leaflets 104 can be coupled to the frame members 118 through the use of heat sealing, solvent bonding, adhesive bonding, or welding the valve leaflets 104 to either a portion of the valve leaflets 104 (i.e., itself) and/or the frame 102.

With respect to coupling the valve leaflets 104 to the first and second openings 138, 140 and the other portions of the valve leaflet connection location 136, the valve leaflets 104 can be passed from the inner surface 170 of the first structural member 112 and wrapped around at least a portion of the outer surface 118 adjacent the first and second openings 138, 140. For example, securing the valve leaflets 104 at the first and second openings 138, 140 can be accomplished by making longitudinal cuts of a predetermined length into the valve leaflets 104 adjacent the first and second openings 138, 140. In one embodiment, each cut creates two flaps adjacent each of the first and second openings 138, 140. The flaps can then pass through the frame adjacent the first and second openings 138, 140 and each of the two resulting flaps can be wrapped from the inner surface 170 around the frame 102 to the outer surface 118. The valve leaflets 104 can then be coupled to itself and/or the frame 102, as described herein. In addition, sutures can be passed through the first and second openings 138, 140 and the valve leaflets 104 so as to secure the valve leaflets 104 to the frame 102. In one embodiment, providing the flaps as described allows for the valve leaflets 104 to create a more fluid tight commissure 154 in the area adjacent the first and second openings 138, 140.

The valve leaflets 104 can have a variety of sizes and shapes. For example, each of the valve leaflets 104 can have a similar size and shape. Alternatively, each of the valve leaflets 104 need not have a similar size and shape (i.e., the valve leaflets can have a different size and shape with respect to each other).

In an additional embodiment, the valve leaflets 104 can include one or more support structures, where the support structures can be integrated into and/or onto the valve leaflets 104. For example, the valve leaflets 104 can include one or more support ribs having a predetermined shape. In one embodiment, the predetermined shape of the support ribs can include a curved bias so as to provide the valve leaflets 104 with a curved configuration. Support ribs can be constructed of a flexible material and have dimensions (e.g., thickness, width and length) and cross-sectional shape that allows the support ribs to be flexible when the valve leaflets 104 are urged into an open position, and stiff when the valve leaflets 104 are urged into a closed position upon experiencing sufficient back flow pressure from the direction downstream from the valve. In an additional embodiment, support ribs can also be attached to frame 102 so as to impart a spring bias to the valve leaflets in either the open or the closed configuration.

As described herein, the valve leaflets 104 can be located over at least the inner surface 170 of the frame 102. FIGS. 1A and 1B illustrate an embodiment of this configuration, where the material of the valve leaflets 104 extends over the inner surface 170 and the outer surface 118 of the first structural member 112 in the valve leaflet connection location 136, as described herein. Numerous techniques may be employed to laminate or bond the material of the valve leaflets 104 on the outer surface 118 and/or the inner surface 170 of the frame 102, including heat setting, adhesive welding, application of uniform force and other bonding techniques. The material of the valve leaflets 104 can also be joined to itself and/or the first structural member 112 according to the methods described in U.S. Patent Application Publication US 2002/0178570 to Sogard et al., which is hereby incorporated by reference in its entirety.

The material can also be coupled to the valve leaflet connection location 136 of the first structural member 112 so as to form the valve leaflets 104, as described herein. In one embodiment, the material for the valve leaflets 104 can be in the form of a sheet or a sleeve of material, as described herein, which can be connected to the frame 102. Alternatively, the material for the valve leaflets 104 can initially be in the form of a liquid that can be used to cast and/or form the valve leaflets 104 over the frame 102. Other forms, including intermediate forms, of the valve leaflets 104 are also possible.

The material of the valve leaflets 104 can be coupled to the valve leaflet connection location 136 of the first structural member 112, including the first and second openings 138, 140, in a variety of ways so as to provide the various embodiments of the valve of the present disclosure. For example, a variety of fasteners can be used to couple the material of the valve leaflets 104 to the frame 102 so as to form the valve 100. Suitable fasteners can include, but are not limited to, biocompatible staples, glues, sutures or combinations thereof. In an additional embodiment, the material of the valve leaflets 104 can be coupled to the frame 102 through the use of heat sealing, solvent bonding, adhesive bonding, or welding the material of the valve leaflets 104 to either a portion of the valve leaflets 104 (i.e., itself) and/or the frame 102.

The valve leaflets 104 may also be treated and/or coated with any number of surface or material treatments. For example, the valve leaflets 104 can be treated with one or more biologically active compounds and/or materials that may promote and/or inhibit endothelization and/or smooth muscle cell growth of the valve leaflets 104. Similarly, the valve leaflets 104 may be seeded and covered with cultured tissue cells (e.g., endothelial cells) derived from a either a donor or the host patient which are attached to the valve leaflets 104. The cultured tissue cells may be initially positioned to extend either partially or fully over the valve leaflets 104.

Valve leaflets 104 can also be capable of inhibiting thrombus formation. Additionally, valve leaflets 104 may either prevent or facilitate tissue ingrowth there through, as the particular application for the valve 100 may dictate. For example, valve leaflets 104 on the outer surface 112 may be formed from a porous material to facilitate tissue ingrowth there through, while valve leaflets 104 on the inner surface 114 may be formed from a material or a treated material which inhibits tissue ingrowth.

FIGS. 3A through 3E provide illustrations of different configurations of the valve frame 302 that have been cut to provide them in a planar view. As illustrated, the valve frame 302 includes the first and second structural members 312, 314 that form the elongate base portion 316 and the bulbous portion 320, respectively. In one embodiment, the first and second structural members 312, 314 of the elongate base portion 316 and the bulbous portion 320 can include a series of interconnected members. These interconnected members, in one embodiment, can act as spring members to help retain the expanded shape of the valve frame 302. In one embodiment, the interconnection of these members allows for the spring force of aligned springs integrated into the frame 302 to be added in series so as to increase the spring force potential of the frame 302.

As illustrated, the first and second structural members 312, 314 can have a number of different configurations that provide the elongate base portion 316 and the bulbous portion 320. As will be appreciated, other configurations are possible that provide the bulbous portion 320 and/or the elongate base portion 316. In addition, the bulbous portion 320 of the valve frame 302 can have a number of different configurations so as to provide the sinus pocket, as discussed herein. For example, the bulbous portion 320 can have one or more of a spherical, semi-spherical, ovoid, semi-ovoid, conical, semi-conical, torus, semi-torus, cylindrical, and semi-cylindrical. In addition, each of two or more of the sinus pockets of the valve frame 302 can have different shapes as discussed herein. In other words, the need not have the same shape as the other sinus pocket of the valve frame 302.

In addition, the first and second structural members 312, 314 can each have two or more cross-sectional shapes and/or two or more different dimensions (e.g., a greater width and depth of the first and second structural members 312, 314 for the portions of the elongate base portion 316 and/or the bulbous portion 320 as compared to the remainder of the elongate base and/or bulbous portion 316, 320.

As illustrated, the valve frame 302 can include the valve leaflet connection region 336 for coupling the valve leaflets. As discussed herein, the valve leaflet connection region 336 can include the first and second opening 338, 340 and the predetermined portion 346 of the first structural member 312.

FIG. 4 illustrates one embodiment of a system 480. System 480 includes valve 400, as described herein, reversibly joined to catheter 482. The catheter 482 includes an elongate body 484 having a proximal end 486 and a distal end 488, where valve 400 can be located between the proximal end 486 and distal end 488. The catheter 482 can further include a lumen 490 longitudinally extending to the distal end 488. In one embodiment, lumen 490 extends between proximal end 486 and distal end 488 of catheter 482. The catheter 482 can further include a guidewire lumen 492 that extends within the elongate body 484, where the guidewire lumen 492 can receive a guidewire for positioning the catheter 482 and the valve 400 within a body lumen (e.g., a vein of a patient).

The system 480 can further include a deployment shaft 494 positioned within lumen 490, and a sheath 496 positioned adjacent the distal end 488. In one embodiment, the valve 400 can be positioned at least partially within the sheath 496 and adjacent the deployment shaft 494. For example, the valve 400 can be fully or partially sheathed with the sheath 496. The deployment shaft 494 can be moved within the lumen 490 to deploy valve 400. For example, deployment shaft 494 can be used to push valve 400 from sheath 496 in deploying valve 400.

Figure 5:
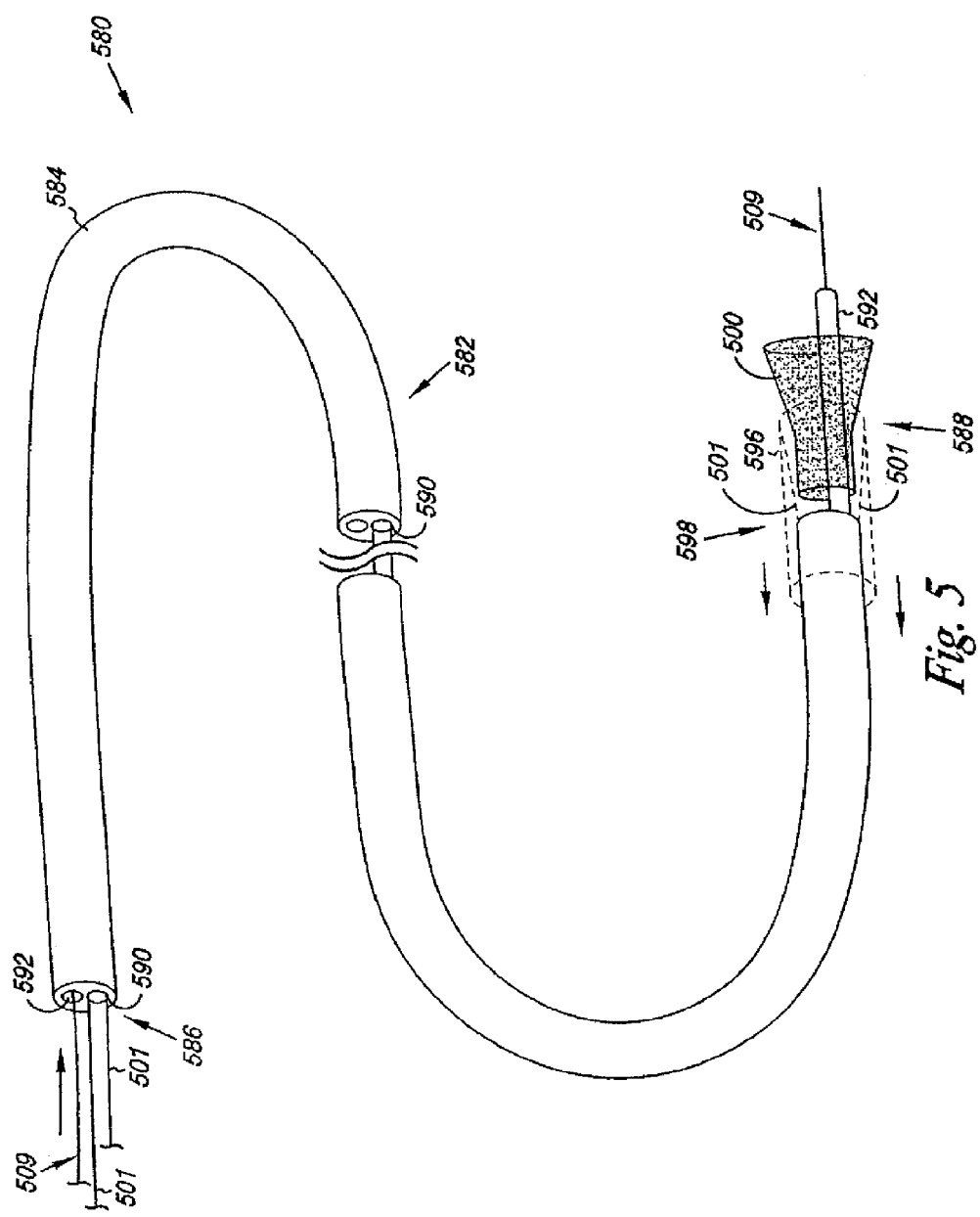
FIG. 5 illustrates an embodiment of a system that includes a valve according to the present disclosure.

FIG. 5 illustrates an additional embodiment of the system 580. The catheter 582 includes elongate body 584, lumen 590, a retraction system 598 and a retractable sheath 596. The retractable sheath 596 can be positioned over at least a portion of the elongate body 584, where the retractable sheath 596 can move longitudinally along the elongate body 584. The valve 500 can be positioned at least partially within the retractable sheath 596, where the retractable sheath 596 moves along the elongate body 596 to deploy the valve 500. For example, the valve 500 can be fully or partially sheathed with the sheath 596.

In one embodiment, retraction system 598 includes one or more wires 501 coupled to the retractable sheath 596, where the wires are positioned at least partially within and extend through lumen 590 in the elongate body 584. Wires of the retraction system 598 can then be used to retract the retractable sheath 596 in deploying valve 500. In one embodiment, a portion of the elongate body 584 that defines the guidewire lumen 592 extends through the lumen 506 of the valve 500 to protect the valve 500 from the movement of the guidewire 509.

Figure 6A:
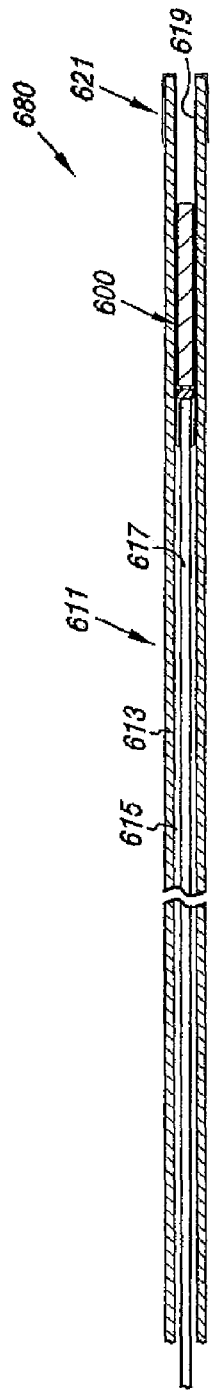
FIGS. 6A, 6B and 6C illustrate an embodiment of a system that includes a valve according to the present disclosure.
Figure 6B:
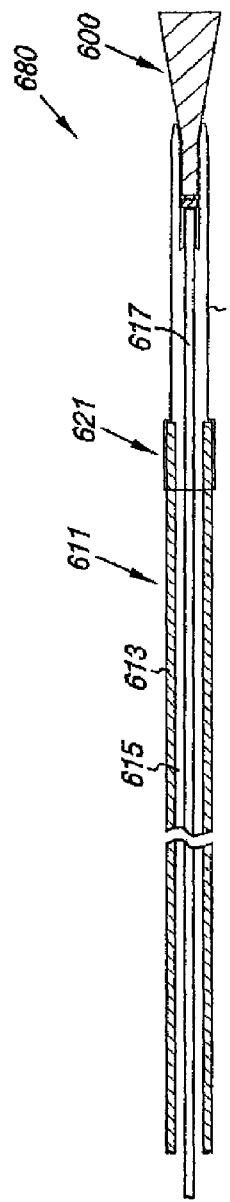
Figure 6C:
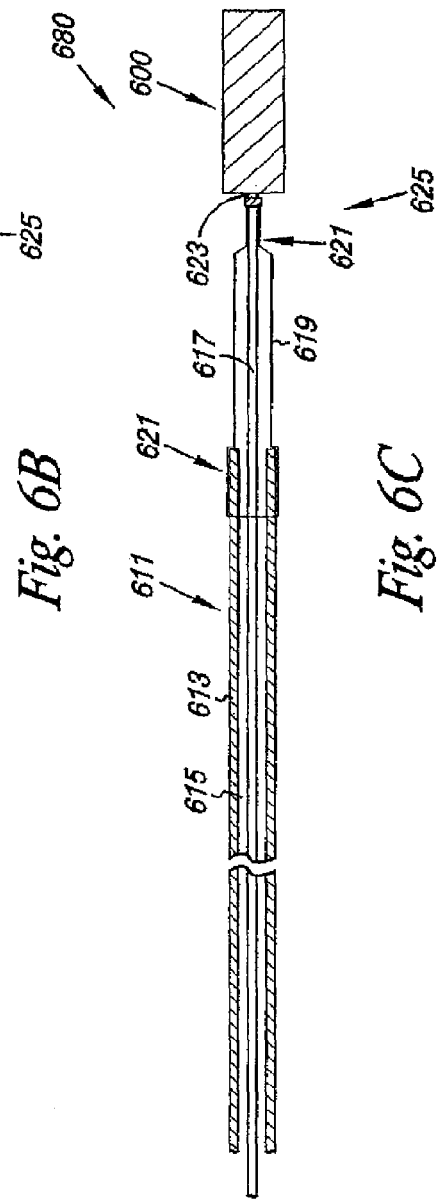

FIGS. 6A-6C illustrate an additional embodiment of the system 680. The system 680 includes a tubular sheath 611 having an elongate body 613 and a lumen 615. The system 680 further includes a delivery shaft 617 positioned within the lumen 615 of the tubular sheath 611. In one embodiment, the tubular sheath 611 and the delivery shaft 617 can move longitudinally relative each other.

In one embodiment, the system 680 includes a flexible cover 619 between the tubular sheath 611 and the delivery shaft 617. In one embodiment, the flexible cover 619 is connected to the tubular sheath 611 and the delivery shaft 617 at a fluid tight seal 621 so as to prevent the transmission of friction from the elongate body 613 to device 600 while the elongate body 613 is retracted during the deployment cycle. In one embodiment, this can be accomplished by creating intentional friction surfaces between the elongate body 613 and flexible cover 619 as is demonstrated in FIG. 6A or two layers of the flexible cover 619 as is demonstrated in FIG. 6B.

In one embodiment, the tubular sheath 611, the delivery shaft 617 and the flexible cover 619 can each be formed from a number of different materials. For the tubular sheath examples include, but are not limited to materials selected from one or more of ePTFE, PTFE, PE, PET, silicone, and polyurethanes. For the delivery shaft 617 examples include, but are not limited to, those selected from a metal, a metal alloy, and/or a polymer. Examples include, but are not limited one or more of ePTFE, PTFE, PE, nylons, PET, silicone, polyurethanes, and stainless steel (e.g., 316L).

In addition, the delivery shaft 617 can also include a configuration that imparts sufficient column rigidity to allow it to be pushed and/or pulled through the lumen 615. For example, the delivery shaft 617 can be formed with reinforcing members bound within the body of the delivery shaft 617 (e.g., an elongate braid of stainless steel co-extruded with a polymer). For the flexible cover 619 examples include, but are not limited to, materials selected from one or more of ePTFE, PTFE, PE, PET, nylons, and polyurethanes. As will be appreciated, other materials and configurations for forming the tubular sheath 611, the delivery shaft 617 and the flexible cover 619 are also possible.

As illustrated in FIGS. 6A-6C, the valve 600 can be positioned over the delivery shaft 615 adjacent a distal end 623 of the delivery shaft 617. In addition, the valve 600 can be held in the same relative location 625 as it is being deployed. As illustrated in FIG. 6A, the valve 600, a portion of the flexible cover 619 and the delivery shaft 617 can be positioned within the lumen 615 of the tubular sheath 611. In one embodiment, the configuration illustrated in FIG. 6A allows the valve 600 to be delivered in its compressed state to a predetermined location in the lumen of the body. Once at the predetermined location, the sheath 611 can then be moved relative the delivery shaft 617. FIG. 6B illustrates a situation where the sheath 611 has been pulled over the valve 600 location 625 and at least partially over the delivery shaft 617.

As illustrated, the flexible cover 619 has a tubular configuration that folds back inside of itself (i.e., its lumen) as the tubular sheath 611 is drawn over the valve 600 and the delivery shaft 617. In one embodiment, the lumen 615 of the sheath 611 can contain a lubricating fluid (e.g., saline) to allow the flexible cover 619 to more easily pass over itself as illustrated. As the tubular sheath 611 continues to be pulled back relative the delivery shaft 617 until the valve 600 is released, as illustrated in FIG. 6C. In one embodiment, the valve 600 can include a self-expanding frame that allows the valve 600 to deploy at location 625 once released.

FIGS. 7A-7C illustrate an additional embodiment of the system 780. The system 780 includes a tubular sheath 711 having an elongate body 713 and a lumen 715. The system 780 further includes a delivery shaft 717 positioned within the lumen 715 of the tubular sheath 711. In one embodiment, the tubular sheath 711 and the delivery shaft 717 can move longitudinally relative each other. In contrast to the system illustrated in FIG. 6A-6C, however, the system 780 does not include the flexible cover. As a result, the illustrated embodiment of system 780 allows for an increase in the size of the inner diameter of the elongate body 713 to be used by the delivery shaft and/or the valve 700 as compared to the elongate body that includes the flexible cover.

In one embodiment, the tubular sheath 711 and the delivery shaft 717 can each be formed from materials and have configurations as discussed herein for FIG. 6A-6C. As illustrated in FIGS. 7A-7C, the valve 700 can be positioned over the delivery shaft 715 adjacent a distal end 723 of the delivery shaft 717. In addition, the valve 700 can be held in the same relative location 725 as it is being deployed. As illustrated in FIG. 7A, the valve 700 and the delivery shaft 717 can be positioned within the lumen 715 of the tubular sheath 711. In one embodiment, the configuration illustrated in FIG. 7A allows the valve 700 to be delivered in its compressed state to a predetermined location in the lumen of the body. Once at the predetermined location, the sheath 711 can then be moved relative the delivery shaft 717. FIG. 7B illustrates a situation where the sheath 711 has been pulled at least partially over the valve 700 at location 725 and at least partially over the delivery shaft 717. As the tubular sheath 711 continues to be pulled back relative the delivery shaft 717 the valve 700 is released, as illustrated in FIG. 7C. In one embodiment, the valve 700 can include a self-expanding frame that allows the valve 700 to deploy at location 725 once released.

The embodiments of the present disclosure further include methods for forming the valve of the present disclosure, as described herein. For example, the valve frame can be formed in a number of different ways. In one embodiment, the valve frame can be formed by cutting a tube of material so as to form the first structural member into the elongate base portion and/or the second structural member into the bulbous portion of the valve frame. Examples of techniques for cutting include laser cutting and/or water jet cutting. Other cutting techniques are also possible. When the first structural member and the second structural member are formed separately, the two portions can be joined by a welding technique, such as laser welding. Other welding or bonding techniques are also possible.

Forming the second structural member into the bulbous portion that radially and longitudinally extends from the first structural member can be accomplished through a variety of techniques. For example, the tube of material that is cut to form the first and second structural members can either be formed with or have a bulbous portion bent into the tube of material. In other words, the tube has the bulbous portion before cutting out the first and second structural members.

Alternatively, the first and second structural members can be cut from the tube. The bulbous portion can then be bent into the second structural members of the valve frame to form the bulbous portion. As discussed herein, forming the bulbous portion can include shaping the first structural member and the second structural member into a predetermined shape, such as elliptical or round. Other shapes for the bulbous portion are also possible.

The valve frame can then be positioned over a mandrel having surfaces that support the elongate base portion and the bulbous portion of the valve frame. Once positioned, the valve frame can then be processed according to the material type used for the frame. For example, the valve frame can be heated on the mandrel to set the shape of the valve frame according to techniques as are known.

The method also includes providing the material in predefined shapes for the valve leaflets. The valve leaflet material is applied and coupled to the valve leaflet connection location of the valve frame, as discussed herein, to provide at least the first leaflet and the second leaflet of the valve having surfaces defining the reversibly sealable opening for unidirectional flow of a liquid through the valve. In one embodiment, the opening defined by the valve leaflets can be configured, as discussed herein, to create a Bernoulli Effect across the valve leaflets.

In one embodiment, coupling the material of the valve leaflets to the venous valve frame includes locating the free edge of the valve leaflets adjacent the bulbous portion to provide both the gap and the sinus pocket between the bulbous portion in the venous valve frame and the valve leaflets. As discussed herein, coupling the material of the valve leaflets to the venous valve frame can include configuring the valve leaflets such that at least the gap between the free edge of the valve leaflets and the bulbous portion in the venous valve frame is maintained as the valve leaflets cycles between their opened and closed position.

In an additional example, the valve can be reversibly joined to the catheter, which can include a process of altering the shape of the valve from a first shape, for example an expanded state, to the compressed state, as described herein. For example, the valve can be reversibly joined with the catheter by positioning valve in the compressed state at least partially within the sheath of the catheter. In one embodiment, positioning the valve at least partially within the sheath of the catheter includes positioning the valve in the compressed state adjacent the deployment shaft of the catheter. In an another embodiment, the sheath of the catheter functions as a retractable sheath, where the valve in the compressed state can be reversibly joined with the catheter by positioning the valve at least partially within the reversible sheath of the catheter. In a further embodiment, the catheter can include an inflatable balloon, where the balloon can be positioned at least partially within the lumen of the valve, for example, in its compressed state.

The embodiments of the valve described herein may be used to replace, supplement, or augment valve structures within one or more lumens of the body. For example, embodiments of the present disclosure may be used to replace an incompetent venous valve and help to decrease backflow of blood in the venous system of the legs.

In one embodiment, the method of replacing, supplementing, and/or augmenting a valve structure can include positioning at least part of the catheter including the valve at a predetermined location within the lumen of a body. For example, the predetermined location can include a position within a body lumen of a venous system of a patient, such as a vein of a leg.

In one embodiment, positioning the catheter that includes the valve within the body lumen of a venous system includes introducing the catheter into the venous system of the patient using minimally invasive percutaneous, transluminal catheter based delivery system, as is known in the art. For example, a guidewire can be positioned within a body lumen of a patient that includes the predetermined location. The catheter, including valve, as described herein, can be positioned over the guidewire and the catheter advanced so as to position the valve at or adjacent the predetermined location.

As described herein, the position of the one or more radiopaque markers can be selected so as to provide information on the position, location and orientation (e.g., axial, directional, and/or clocking position) of the valve during its implantation. For example, radiopaque markers can be configured radially and longitudinally on predetermined portions of the valve frame and/or the elongate body of the catheter to indicate not only a longitudinal position, but also a radial position of the valve leaflets and the valve frame (referred to as a clock position). In one embodiment, the radiopaque markers are configures to provide radiographic images that indicate the relative radial position of the valve and valve leaflets on the catheter.

Figure 8A:
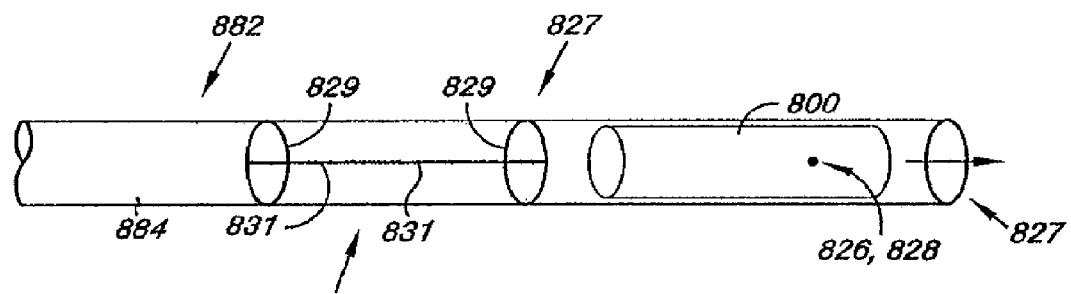
FIGS. 8A, 8B and 8C illustrate an embodiment of a system that includes a valve and a catheter having radiopaque markers according to the present disclosure.
Figure 8B:
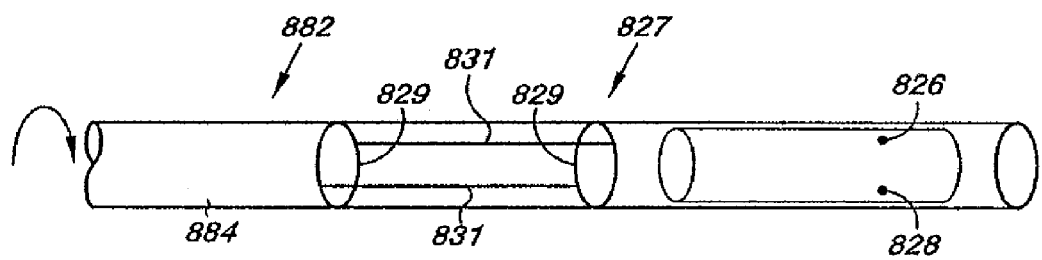
Figure 8C:
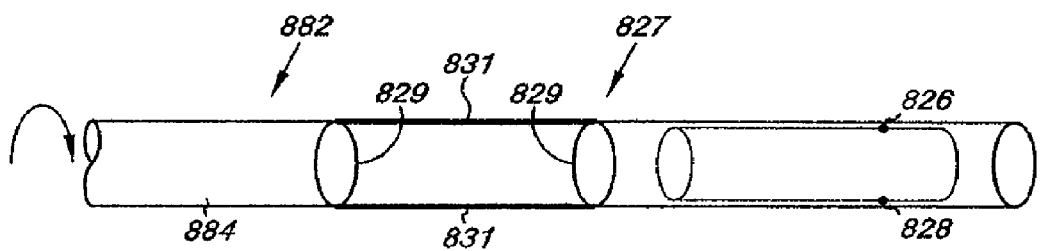

FIGS. 8A-8C provide an illustration of the radiopaque markers 827 associated with the elongate body 884 of the catheter 882. As illustrated, the radiopaque markers 827 include a radial component 829 and a longitudinal component 831. Depending upon the radial position of the catheter 882, the radiopaque markers 827 can provide a different and distinguishable radiographic image. For example, in a first position 833 illustrated in FIG. 8A the longitudinal component 831 of the radiopaque markers 827 are aligned so as to overlap. As the catheter 882 is rotated, as illustrated in FIGS. 8B and 8C, the radiographic image of the radial component 829 and/or longitudinal component 831 of the radiopaque markers 827 changes.

The change in the relationship of the radial and longitudinal components 829, 831 as the catheter 882 is rotated allows for the relative position of the valve 800, valve frame and valve leaflets to be determined from the radiographic image. For example, the relative position of the first and second leaflet connection regions 826, 828 could be aligned with longitudinal component 831 of the radiopaque markers 827. This would allow the clock position for the valve 800 to be determined so that the valve can be positioned in a more natural orientation relative the compressive forces the valve will experience in situ. In other words, the allowing for clocking of the valve 800 as described herein allows the valve to be radially positioned in same orientation as native valve that it's replacing and/or augmenting.

As will be appreciated, other relative relationships between the radiopaque markers 827 and the position of the valve 800 on the catheter 882 are possible. So, embodiments of the present disclosure should not be limited to the present example. For example, additional radiopaque markers 827 on the valve 800 could be used either alone or in combination with radiopaque markers 827 on the catheter 882 to help in positioning the valve 800 within a lumen.

The valve can be deployed from the catheter at the predetermined location in a number of ways, as described herein. In one embodiment, valve of the present disclosure can be deployed and placed in a number of vascular locations. For example, valve can be deployed and placed within a major vein of a patient's leg. In one embodiment, major veins include, but are not limited to, those of the peripheral venous system. Examples of veins in the peripheral venous system include, but are not limited to, the superficial veins such as the short saphenous vein and the greater saphenous vein, and the veins of the deep venous system, such as the popliteal vein and the femoral vein.

As described herein, the valve can be deployed from the catheter in a number of ways. For example, the catheter can include the retractable sheath in which valve can be at least partially housed, as described herein. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft, as described herein. Valve can be deployed by moving the deployment shaft through the catheter to deploy valve from the sheath, where the valve self-expands to be positioned at the predetermined location. In an additional embodiment, the valve can be deployed through the use of an inflatable balloon.

Once implanted, the valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

In addition, the use of both the bulbous portion and/or elongate base portion of the valve can provide a self centering aspect to valve within a body lumen. In one embodiment, the self centering aspect resulting from the bulbous portion and/or elongate base portion of the valve may allow valve to maintain a substantially coaxial alignment with the body lumen (e.g., such as a vein) as valve leaflets deflect between the open and closed configurations so as to better seal the reversible opening when valve is closed.

While the present disclosure has been shown and described in detail above, it will be clear to the person skilled in the art that changes and modifications may be made without departing from the scope of the disclosure. As such, that which is set forth in the foregoing description and accompanying drawings is offered by way of illustration only and not as a limitation. The actual scope of the disclosure is intended to be defined by the following claims, along with the full range of equivalents to which such claims are entitled.

In addition, one of ordinary skill in the art will appreciate upon reading and understanding this disclosure that other variations for the disclosure described herein can be included within the scope of the present disclosure. For example, the frame 102 and/or the valve leaflets 104 can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A valve comprising:
   a first structural member that defines an elongate base portion having a first end, a second end, and an outer surface concentrically arranged relative a longitudinal axis, wherein the outer surface provides at least two points of a perimeter of a first elliptical plane orthogonal to and passing through the longitudinal axis, and wherein the first structural member at each of the first end and the second end includes a first curve and a second curve opposite the first curve with the first curve and the second curve of the first end positioned radially orthogonal to the first curve and the second curve of the second end of the base portion;
   a second structural member that extends between the first end and the second end of the elongate base portion to define a bulbous portion, wherein the outer surface of the elongate base portion and the second structural member provide at least four points of a perimeter of a plane orthogonal to the longitudinal axis, wherein the plane has an area that is greater than the area of the first elliptical plane;

a valve leaflet connection location along the first structural member of the venous valve frame; and at least two valve leaflets, each leaflet connected to the valve leaflet connection location.

2. The valve of claim 1, wherein the perimeter of the plane for the bulbous portion-defines an elliptical shape.

3. The valve of claim 2, wherein the first structural member defines a first axis of the elliptical shape and the second structural member defines a second axis of the elliptical shape that is twenty percent (20%) to fifty percent (50%) greater than the first axis.

4. The valve of claim 2, wherein the first structural member defines a first axis of the elliptical shape and the second structural member defines a second axis of the elliptical shape that is one (1) to four (4) millimeters greater than the length of the first axis.

5. The valve of claim 1, wherein the perimeter of the plane for the bulbous portion defines a round shape.

6. The valve of claim 1, wherein the first curve and the second curve flare away from a center longitudinal axis.

7. The valve of claim 1, wherein the first structural member includes surfaces defining a first opening and a second opening for the valve leaflet connection location, wherein the first and second openings are adjacent a region of the bulbous portion of the valve frame and positioned opposite each other along a common axis.

8. The valve of claim 1, wherein the first elliptical plane is a circular plane.

9. The valve of claim 1, wherein the at least two valve leaflets and the bulbous portion define a sinus pocket.

10. A system comprising:
a delivery catheter defining a lumen;
a valve joined to the delivery catheter, the valve comprising:
 a first structural member that defines an elongate base portion having a first end, a second end, and an outer surface concentrically arranged relative a longitudinal axis, wherein the outer surface provides at least two points of a perimeter of a first elliptical plane orthogonal to and passing through the longitudinal axis, and wherein the first structural member at each of the first end and the second end includes a first curve and a second curve opposite the first curve with the first curve and the second curve of the first end positioned radially orthogonal to the first curve and the second curve of the second end of the base portion;
 a second structural member that extends between the first end and the second end of the elongate base portion to define a bulbous portion, wherein the outer surface of the elongate base portion and the second structural member provide at least four points of a perimeter of a plane orthogonal to the longitudinal axis, wherein the plane has an area that is greater than the area of the first elliptical plane;
 a valve leaflet connection location along the first structural member of the venous valve frame; and
 at least two valve leaflets, each leaflet connected to the valve leaflet connection location;
a deployment shaft disposed within the lumen of the catheter; and
a sheath positioned at a distal end of the catheter, the valve configured to be at least partially positioned within the sheath.

* * * * *